United States Patent
Andjelic et al.

(10) Patent No.: US 8,450,431 B2
(45) Date of Patent: May 28, 2013

(54) BIOABSORBABLE POLYMER COMPOSITIONS EXHIBITING ENHANCED CRYSTALLIZATION AND HYDROLYSIS RATES

(75) Inventors: Sasa Andjelic, Nanuet, NY (US); Benjamin D. Fitz, Brooklyn, NY (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 13/567,813

(22) Filed: Aug. 6, 2012

(65) Prior Publication Data
US 2012/0302528 A1    Nov. 29, 2012

Related U.S. Application Data

(60) Division of application No. 12/107,569, filed on Apr. 22, 2008, now Pat. No. 8,236,904, which is a continuation-in-part of application No. 11/320,029, filed on Dec. 28, 2005, now abandoned.

(51) Int. Cl.
*C08L 67/04* (2006.01)

(52) U.S. Cl.
USPC .......................... 525/411; 525/410; 525/415

(58) Field of Classification Search
USPC .......................................... 525/411, 410, 415
See application file for complete search history.

(56) References Cited

U.S. PATENT DOCUMENTS

| | | | |
|---|---|---|---|
| 3,551,361 A | 12/1970 | Needham | |
| 4,052,988 A | 10/1977 | Doddi et al. | |
| 4,098,845 A | 7/1978 | Keck | |
| 4,163,100 A | 7/1979 | Bier et al. | |
| 4,208,215 A | 6/1980 | Kleiner et al. | |
| 4,400,328 A | 8/1983 | Takegami et al. | |
| 4,444,927 A | 4/1984 | Borysko | |
| 4,490,326 A | 12/1984 | Beroff et al. | |
| 4,495,166 A | 1/1985 | Calvert et al. | |
| 4,720,570 A | 1/1988 | Boyle | |
| 4,906,730 A | 3/1990 | Takekoshi et al. | |
| 4,972,016 A | 11/1990 | Murakami | |
| 5,155,183 A | 10/1992 | Arnold, III et al. | |

(Continued)

FOREIGN PATENT DOCUMENTS

| | | |
|---|---|---|
| JP | 57198745 | 12/1985 |
| JP | 02022359 | 1/1990 |

(Continued)

OTHER PUBLICATIONS

English translation of JP2005-146425 A Sep. 6, 2005.

(Continued)

*Primary Examiner* — Alicia Toscano
(74) *Attorney, Agent, or Firm* — Roberts Mlotkowski Safran & Cole, P.C.

(57) ABSTRACT

A bimodal bioabsorbable polymer composition. The composition includes a first amount of a bioabsorbable polymer polymerized so as to have a first molecular weight distribution; a second amount of said bioabsorbable polymer polymerized so as to have a second molecular weight distribution having a weight average molecular weight between about 10,000 to about 50,000 Daltons, the weight average molecular weight ratio of said first molecular weight distribution to said second molecular weight distribution is at least about two to one; wherein a substantially homogeneous blend of said first and second amounts of said bioabsorbable polymer is formed in a ratio of between about 50/50 to about 95/5 weight/weight percent. Also disclosed are a medical device, a method of making a medical device and a method of melt blowing a semi-crystalline polymer blend.

14 Claims, 12 Drawing Sheets

U.S. PATENT DOCUMENTS

| | | | |
|---|---|---|---|
| 5,266,629 | A | 11/1993 | Weinkauf et al. |
| 5,281,643 | A | 1/1994 | Natarajan |
| 5,344,982 | A | 9/1994 | Hergenrother et al. |
| 5,359,013 | A | 10/1994 | Mason et al. |
| 5,414,036 | A | 5/1995 | Gilmer |
| 5,414,051 | A | 5/1995 | Mason et al. |
| 5,431,972 | A | 7/1995 | Richeson et al. |
| 5,496,918 | A | 3/1996 | Khanna et al. |
| 5,539,076 | A | 7/1996 | Nowlin et al. |
| 5,702,826 | A | 12/1997 | Ehret et al. |
| 5,723,520 | A | 3/1998 | Akkapeddi et al. |
| 5,830,493 | A | 11/1998 | Yokota |
| 5,856,386 | A | 1/1999 | Sakai et al. |
| 5,969,021 | A | 10/1999 | Reddy et al. |
| 6,080,798 | A | 6/2000 | Handa et al. |
| 6,159,406 | A | 12/2000 | Shelby et al. |
| 6,302,958 | B1 | 10/2001 | Lindrud et al. |
| 6,319,576 | B1 | 11/2001 | Rule et al. |
| 6,444,044 | B1 | 9/2002 | Beckett et al. |
| 6,488,938 | B1 | 12/2002 | Ogura et al. |
| 6,506,809 | B2 | 1/2003 | Hrivnak |
| 6,521,685 | B1 | 2/2003 | Zhao |
| 6,521,717 | B1 | 2/2003 | Itoh |
| 6,534,623 | B1 | 3/2003 | Gochanour |
| 6,794,484 | B2 | 9/2004 | Newman, Jr. et al. |
| 6,831,149 | B2 | 12/2004 | Newman, Jr. et al. |
| 2004/0022859 | A1 | 2/2004 | Chen et al. |
| 2004/0094300 | A1 | 5/2004 | Sullivan et al. |
| 2005/0124941 | A1 | 6/2005 | Panchula et al. |
| 2006/0084340 | A1 | 4/2006 | Bond et al. |

FOREIGN PATENT DOCUMENTS

| | | |
|---|---|---|
| JP | 2155905 | 6/1990 |
| JP | 6207098 | 7/1994 |
| JP | 7166038 | 6/1995 |
| JP | 7196675 | 8/1995 |
| JP | 08003432 | 1/1996 |
| JP | 2000045164 | 2/2000 |
| JP | 2001288154 | 10/2001 |
| JP | 2005-146425 A | 6/2005 |
| WO | 92/07905 | 5/1992 |
| WO | 01/61345 | 8/2001 |
| WO | 03/075975 A1 | 9/2003 |
| WO | 2004/011054 A2 | 2/2004 |
| WO | 2004/011054 A3 | 2/2004 |
| WO | 2004/043432 A2 | 5/2004 |
| WO | 2007/078718 | 7/2007 |

OTHER PUBLICATIONS

International Search Report for International Application No. PCT/US2006/047339 dated Apr. 6, 2007.

International Search Report for International Application No. PCT/US2009/041269 dated Oct. 29, 2009.

Stephen Z.D. Cheng and Bernhard Wunderlich, "Molecular Segregation and Nucleation of Poly(ethylene Oxide) Crystallized from the Melt. II. Kinetic Study", Department of Chemistry, Rensselear Polytechnic Institute, Troy, New York 12181, 1985.

J.M. Rego Lopez, M.T. Conde Frana, B. Terselius and U.W. Gedde, "Crystallization of binary linear polyethylene blends", Department of Polymer Technology, The Royal Institute of Technology, S-100 44 Stockholm, Sweden, 1988.

L. Minkova and M. Mihailov, "Kinetics of nonisothermal crystallization and melting of normal high density and ultra-high molecular weight polyethylene blends", Central Laboratory for Polymers, Bulgarian Academy Sciences, Sofia, Bulgaria, 1989.

Stephen Z.D. Cheng, Jeffrey S. Barley and Ernst D. Von Meerwall, "Self-Diffusion of Poly(ethylene Oxide) Fractions and Its Influence on the Crystalline Texture", Institute and Departments of Polymer Science, and Physics, College of Polymer Science and Polymer Engineering, The University of Akron, Akron, Ohio 443, 1989.

C. Migliaresi, A. De Lollis, L Fambri & D. Cohn, "The Effect of Thermal History on the Crystallinity of Different Molecular Weight PLLA Biodegradable Polymers", Dipartimento di Ingegneria dei Materiali, Universita di Trento, via Mesiano 77, 38050 Trento, Italy et al., 1991.

Horst A. Von Recum, Robert L. Cleek, Suzanne G. Eskin and Antonios G. Mikos, "Degradation of polydispersed poly(L-lactic acid) to modulate lactic acid release", Department of Chemical Engineering and Institute of Biosciences and Bioengineering Cox Laboratory for Biomedical Engineering, Rice University, P.O. Box 1982, Houston, TX 77251 et al., 1995.

Scott C. Schmidt and Marc A. Hillmyer, "Polylactide Stereocomplex Crystallites as Nucleating Agents for Isotactic Polylactice", Department of Chemistry, University of Minnesota, Minneapolis, MN 55455, 2001.

H.Yamane and K. Sasai, Effect of the addition of poly(D-lactic acid) on the thermal property of poly(L-lactic acid), Graduate School of Science and Technology, Kyoto Institute of Technology, Matsugasaki, Sakyo-ku, Kyoto 606-8585, Japan, 2003.

BIOABSORBABLE POLYMER COMPOSITIONS EXHIBITING ENHANCED CRYSTALLIZATION AND HYDROLYSIS RATES

CROSS-REFERENCE TO RELATED APPLICATION

This application is a Divisional of U.S. application Ser. No. 12/107,569 filed Apr. 22, 2008 now U.S. Pat. No. 8,236,904, which is a Continuation-in-Part of application Ser. No. 11/320,029 filed on Dec. 28, 2005 now abandoned, the contents of which are hereby incorporated by reference in their entirety.

FIELD

This invention relates to absorbable polymer compositions and, more particularly, to bioabsorbable polymer compositions having a bimodal molecular weight distribution, to medical devices produced therefrom and to methods of making bioabsorbable polymer compositions.

BACKGROUND

In polymeric crystals, polymer chains are arranged in a two-dimensional pattern. Due to statistical and mechanical requirements, a complete polymer chain cannot form a single straight stem, the straight stems being limited to a certain length depending on the crystallization temperature. As a result thereof, the stems fold and reenter into a lattice. This reentry can be adjacent to the previous stem or at a random lattice point. The perfectly ordered portion of a polymer is crystalline and the folded surface is amorphous. As such, polymers are semi-crystalline. The crystalline portion may occur either in isolation or as an aggregate with other similar crystals leading to the formation of mats or bundles or spherulites.

The first step in the formation of spherulites, wherein a straight stem of a polymer chain called a nucleus forms from a random coil, is called nucleation. The rest of the process that includes lamellae growth and spherulite formation is cumulatively called crystal growth. In general, single crystals take the form of thin lamellae that are relatively large in two dimensions and bounded in the third dimension by the folds. Typically all the lamellae within one spherulite originate from a single point. As the spherulite grows, the lamellae get farther and farther apart. When the distance between two lamellae reaches a critical value, they tend to branch. Since the growth process is isotropic, the spherulites have a circular shape in two dimensions and a spherical shape in three dimensions for solidification in a uniform thermal field.

A certain degree of crystallinity is often desired during injection molding or extrusion operations due to the higher thermal and mechanical stability associated therewith. If the crystallization rate is slow or uneven, the resultant product properties may have a wide variation in morphology, creating a potential for lines of imperfection that may lead to material failure and result in lower production capacity and reduced quality of the final product.

Absorbable polymers are known to be generally slow crystallizing materials. As is well known to those skilled in the art, poly(L-lactic acid) (PLLA) belongs to the group of very slow crystallizable polyesters. High molecular weight PLLA crystallizes with even more difficulty, due to the reduced mobility of its highly entangled macromolecules. The crystallinity of different molecular weight PLLA polymers (18,000, 31,000, 156,000 and 425,000 g/mol) has been studied by calorimetric methods (see: *Clinical Materials,* 1991, 8(1-2), 111. As demonstrated by that study, during cooling from the melt (rate=−0.5° C./min), only the lower molecular weight polymers were able to develop any measurable crystallinity.

In order to increase the rate of crystallization of a polymer, one must increase either the steady-state concentration of nuclei in the polymer matrix, or increase the rate of crystal growth. In general, an increase in nucleation density can be readily accomplished by adding nucleating agents that are either physical (inactive) or chemical (active) in nature. An introduction of foreign particles can also serve as a nucleation agent. For example, with regard to the absorbable polymers used by the medical industry, such agents can include starch, sucrose, lactose, fine polymer particles of polyglycolide and copolymers of glycolide and lactide, which may be used during manufacturing of surgical fasteners or during subsequent fiber processing. Other ways to increase the nucleation rate without the addition of foreign-based materials include copolymerization with a stiffer, highly crystallizable component, preserving nucleating seeds of a faster crystallizing component during melt manufacturing steps, stress induced nucleation, the use of magnetic field strength or sonic-based energy, as used by the pharmaceutical industry, and the use of specific ratios of mono- to bi-functional initiators in the ring-opening polymerization of glycolide-containing absorbable copolyesters.

With regard to the absorbable polymers having utility in the area of wound management, improved hydrolysis characteristics are often desired to reduce the incidence of infection and increase patient comfort. Improved hydrolysis characteristics are also desired in the area of drug delivery to enhance drug release.

In order to control or increase the bioabsorption/hydrolysis rate of absorbable polymers, several approaches have been proposed. These include exposure to high-energy radiation, such as gamma rays or electron beam radiation treatment under an oxygen atmosphere, blending or copolymerizing the absorbable slow degrading polymer with a faster absorbing material, use of a pore-forming component, varying the pH value of materials having pH sensitive groups and addition of monomers or oligomers to the polymer matrix.

It has been proposed in U.S. Pat. No. 5,539,076 that bimodal molecular weight distributions may be employed for polyolefins to enhance polymer processing, reduce the tendency of die-lip polymer buildup and smoking in on-line operations. Moreover, the crystallization behavior of various binary compositions has been reported for linear polyethylene blends in *Polymer,* 1998, 29(6), 1045. This study suggests that the two fractions of a binary linear polyethylene blend crystallize separately and independently at moderate and high temperatures and partially co-crystallize at lower temperatures. Similarly, Cheng and Wunderlich, in *J. Polym. Sci. Polym. Phys.,* 1986, 24, 595 and *J. Polym. Sci. Polym. Phys.,* 1991, 29, 515, reported on their crystallization kinetic studies of fractions of poly(ethylene oxides) between 3,500 and 100,000 Mw and their binary mixtures from the melt. These studies suggested that mixed-crystal formation at low crystallization temperatures occurred, with increasing segregation at higher temperatures, despite the higher deposition probabilities of the low molecular weight component.

Von Recum, H. A, Cleek, R. L., Eskint, S. G., and Mikos, A. G., in *Biomaterials* 18, 1995, 441-447, suggested that modulating lactic acid release during in vivo degradation of PLLA implants, by adjusting the polymer polydispersity, was feasible. In their work, polydispersed PLLA membranes comprised of blends of monodispersed PLLA of weight average molecular weight of 82500 and 7600 Daltons were fabricated to investigate the effect of polydispersity on degradation characteristics. The PLLA blends exhibited large spherulites of high molecular weight chains embedded in a low molecular weight matrix. During degradation in a phosphate buffer, the release rate of lactic acid increased as the percentage of the low molecular weight component in the blend was increased. For low molecular weight compositions larger than 50%, voids were created in the degrading blends due to the degradation of low molecular weight chains and the concurrent dissolution of lactic acid, and also the release of undegraded particles of high molecular weight.

Despite these advances in the art, there is still a need for improved absorbable polymers having increased crystallization and/or hydrolysis rates. Thus, it would be desirable to provide advanced absorbable polymers having increased crystallization and/or hydrolysis rates and methods for their production.

SUMMARY

Disclosed herein are compositions and methods of enhancing the crystallization and/or hydrolysis rates for absorbable materials. Also disclosed are methods of preparation of absorbable polymer compositions, the compositions so prepared possessing significantly higher crystallization kinetics and/or hydrolysis rates, and devices produced from such compositions. More specifically disclosed herein are absorbable polymeric blend compositions, processes of making the absorbable polymeric blend compositions and medical devices produced from such absorbable polymeric blend compositions.

In one aspect, provided is a bimodal polymer composition, comprising: a first amount of a bioabsorbable polymer having a first molecular weight distribution; and a second amount of the bioabsorbable polymer having a second molecular weight distribution having a weight average molecular weight between about 10,000 to about 50,000 Daltons, the weight average molecular weight ratio of the first molecular weight distribution to the second molecular weight distribution being at least about two to one; wherein a substantially homogeneous blend of the first and second amounts of the bioabsorbable polymer is formed in a ratio of between about 50/50 to about 95/5 weight/weight percent.

In another aspect, provided is a medical device produced from a process comprising the step of injection molding or extruding the medical device from a bimodal polymer composition or the step of subjecting a medical device made from the bimodal polymer composition to a heat treatment step, the bimodal polymer composition comprising: a first amount of a bioabsorbable polymer polymerized so as to have a first molecular weight distribution; and a second amount of the bioabsorbable polymer polymerized so as to have a second molecular weight distribution having a weight average molecular weight between about 10,000 to about 50,000 Daltons, the weight average molecular weight ratio of the first molecular weight distribution to the second molecular weight distribution being at least about two to one; wherein a substantially homogeneous blend of the first and second amounts of the bioabsorbable polymer is formed in a ratio of between about 50/50 to about 95/5 weight/weight percent.

In yet another aspect, provided is a medical device produced from a process comprising the step of injection molding or extruding the medical device from a bimodal polymer composition or the step of subjecting a medical device made from the bimodal polymer composition to a heat treatment step; the bimodal polymer composition comprising: a first amount of a poly(L-lactide) polymer having a first molecular weight distribution between about 100,000 to about 2,000,000 Daltons; and a second amount of a poly(L-lactide) polymer having a second molecular weight distribution having a weight average molecular weight between about 10,000 to about 50,000 Daltons, the weight average molecular weight ratio of the first molecular weight distribution to the second molecular weight distribution is at least about two to one; wherein a substantially homogeneous blend of the first and second amounts of the bioabsorbable polymer is formed in a ratio of between about 60/40 to 80/20 weight/weight percent; over a temperature range of between about 85° C. to about 150° C.

In still yet another aspect, provided is a medical device produced from a process comprising the step of injection molding or extruding the medical device from a bimodal polymer composition or the step of subjecting a medical device made from the bimodal polymer composition to a heat treatment step; the bimodal polymer composition comprising: a first amount of a poly(dioxanone) polymer having a first molecular weight distribution between about 50,000 to about 100,000 Daltons; and a second amount of a poly(dioxanone) polymer having a second molecular weight distribution having a weight average molecular weight between about 10,000 to about 50,000 Daltons, the weight average molecular weight ratio of the first molecular weight distribution to the second molecular weight distribution is at least about two to one; wherein a substantially homogeneous blend of the first and second amounts of the bioabsorbable polymer is formed in a ratio of between about 60/40 to 95/5 weight/weight percent; over a temperature range of between about 40° C. to about 80° C.

In a further aspect, provided is a method of making a medical device, comprising the step of injection molding or extruding the medical device from a bimodal polymer composition or the step of subjecting a medical device made from the bimodal polymer composition to a heat treatment step, the polymer composition, comprising: a first amount of a bioabsorbable polymer polymerized so as to have a first molecular weight distribution; a second amount of the bioabsorbable polymer polymerized so as to have a second molecular weight distribution having a weight average molecular weight between about 10,000 to about 50,000 Daltons, the weight average molecular weight ratio of the first molecular weight distribution to the second molecular weight distribution being at least about two to one; wherein a substantially homogeneous blend of the first and second amounts of the bioabsorbable polymer is formed in a ratio of between about 60/40 to 95/5 weight/weight percent.

In a still further aspect, provided is a method of making a medical device, comprising the step of injection molding or extruding the medical device from a bimodal polymer composition or the step of subjecting a medical device made from the bimodal polymer composition to a heat treatment step; the bimodal polymer composition comprising: a first amount of a poly(L-lactide) polymer having a first molecular weight distribution between about 100,000 to about 1,000,000 Daltons; and a second amount of a poly(L-lactide) polymer having a second molecular weight distribution having a weight average molecular weight between about 10,000 to about 50,000 Daltons, the weight average molecular weight ratio of the first molecular weight distribution to the second molecular weight distribution is at least about two to one; wherein a substantially homogeneous blend of the first and second amounts of the bioabsorbable polymer is formed in a ratio of between about 60/40 to 80/20 weight/weight percent; over a temperature range of between about 85° C. to about 150° C.

In a yet still further aspect, provided is a method of making a medical device, comprising the step of injection molding or extruding the medical device from a bimodal polymer composition or the step of subjecting a medical device made from the bimodal polymer composition to a heat treatment step; the bimodal polymer composition comprising: a first amount of a poly(dioxanone) polymer having a first molecular weight distribution between about 50,000 to about 100,000 Daltons; and a second amount of a poly(dioxanone) polymer having a second molecular weight distribution having a weight average molecular weight between about 10,000 to about 50,000 Daltons, the weight average molecular weight ratio of the first molecular weight distribution to the second molecular weight distribution is at least about two to one; wherein a substantially homogeneous blend of the first and second amounts of the bioabsorbable polymer is formed in a ratio of between about 60/40 to 95/5 weight/weight percent; over a temperature range of between about 40° C. to about 80° C.

In another aspect, provided is a bimodal polymer composition. The bimodal polymer composition includes a first amount of a fully amorphous bioabsorbable polymer having a first hydrolysis rate and a first molecular weight distribution; and a second amount of the fully amorphous bioabsorbable polymer having a second hydrolysis rate and a second molecular weight distribution having a weight average molecular weight between about 10,000 to about 50,000 Daltons, the weight average molecular weight ratio of the first molecular weight distribution to the second molecular weight distribution is at least about two to one; wherein a substantially homogeneous blend of the first and second amounts of the fully amorphous bioabsorbable polymer is formed in a ratio of between about 50/50 to about 95/5 weight/weight percent, the substantially homogeneous blend having a hydrolysis rate greater than each of the first hydrolysis rate and the second hydrolysis rate.

In yet another aspect, provided is a method of melt blowing a semi-crystalline polymer blend. The method includes the steps of melt blending in an extruder to form a polymer blend a first amount of a bioabsorbable polymer having a first molecular weight distribution; and a second amount of the bioabsorbable polymer having a second molecular weight distribution having a weight average molecular weight between about 10,000 to about 50,000 Daltons, the weight average molecular weight ratio of the first molecular weight distribution to the second molecular weight distribution is at least about two to one; wherein a substantially homogeneous blend of the first and second amounts of the bioabsorbable polymer is formed in a ratio of between about 50/50 to about 95/5 weight/weight percent; extruding the polymer blend through a die assembly, the die assembly having a plurality of spinnerets, to form filament strands; attenuating the filament strands with hot air to form microfibers; collecting the microfibers on a collector screen; and cooling and solidifying the microfibers to form a nonwoven web.

In still yet another aspect, provided is a composition comprising a drug delivery carrier comprising a first amount of a fully amorphous bioabsorbable polymer having a first hydrolysis rate and a first molecular weight distribution; and a second amount of said fully amorphous bioabsorbable polymer having a second hydrolysis rate and a second molecular weight distribution having a weight average molecular weight between about 10,000 to about 50,000 Daltons, the weight average molecular weight ratio of said first molecular weight distribution to said second molecular weight distribution is at least about two to one; and a pharmaceutically active agent, wherein a substantially homogeneous blend of said first and second amounts of said fully amorphous bioabsorbable polymer is formed in a ratio of between about 50/50 to about 95/5 weight/weight percent, said substantially homogeneous blend having a hydrolysis rate greater than each of said first hydrolysis rate and said second hydrolysis rate.

In a further aspect, provided is a nonwoven construct comprising a bimodal polymer composition, comprising a first amount of a fully amorphous bioabsorbable polymer having a first hydrolysis rate and a first molecular weight distribution; and a second amount of the fully amorphous bioabsorbable polymer having a second hydrolysis rate and a second molecular weight distribution having a weight average molecular weight between about 10,000 to about 50,000 Daltons, the weight average molecular weight ratio of the first molecular weight distribution to the second molecular weight distribution is at least about two to one; wherein a substantially homogeneous blend of the first and second amounts of the fully amorphous bioabsorbable polymer is formed in a ratio of between about 50/50 to about 95/5 weight/weight percent, the substantially homogeneous blend having a hydrolysis rate greater than each of the first hydrolysis rate and the second hydrolysis rate, and the nonwoven construct comprising microfibers having a diameter ranging from 1 to 8 µm

BRIEF DESCRIPTION OF THE DRAWINGS

The invention will now be described in more detail with reference to the forms herein disclosed, given only by way of example, and with reference to the accompanying drawings, in which.

DETAILED DESCRIPTION

Figure 1:
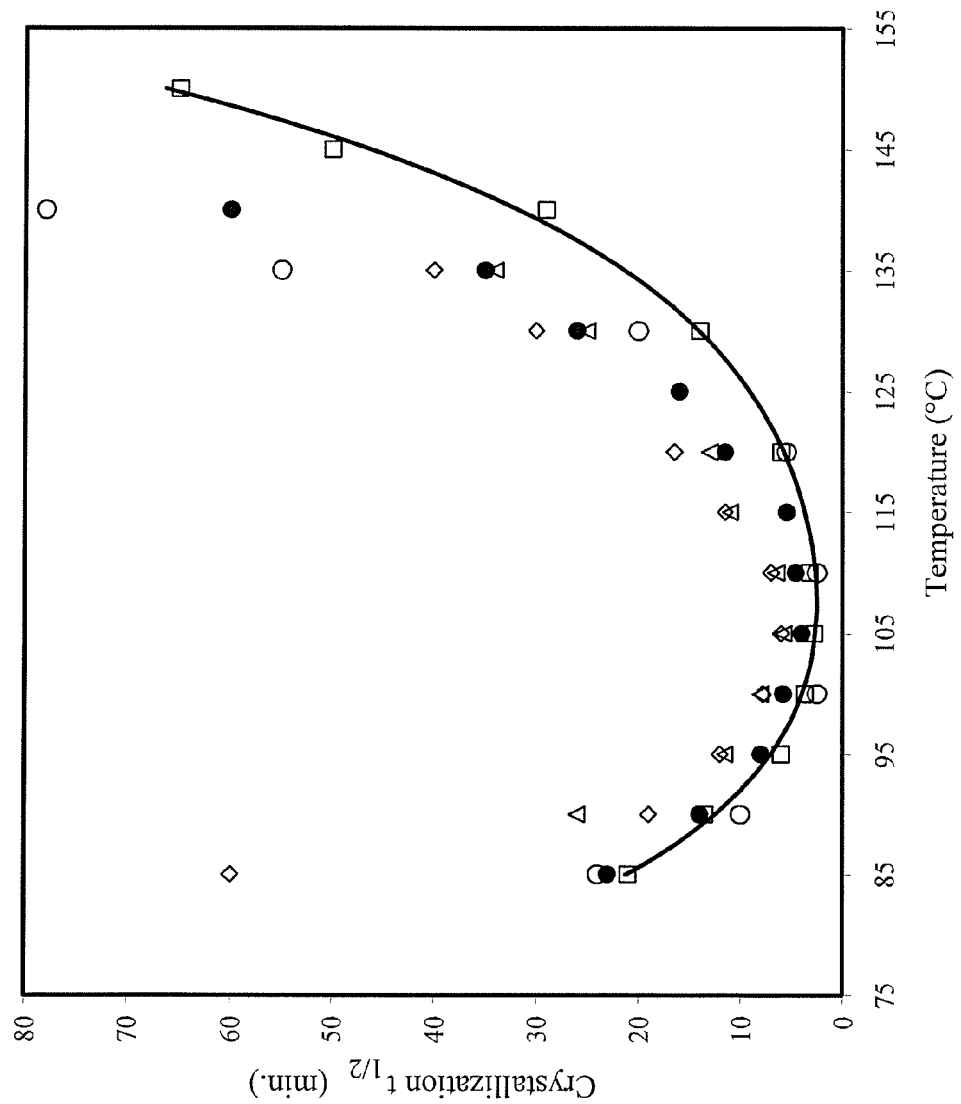
FIG. 1 presents a plot of crystallization rate (expressed as $t_{1/2}$) as a function of crystallization temperature for several PLLA homopolymers, as determined by differential scanning calorimetry (DSC) measurements.

The compositions described herein provide significantly higher crystallization rates over the crystallization rates of the individual components. Additionally, the compositions described herein provide significantly higher rates of hydrolysis over the rates of hydrolysis of the individual components of those compositions. The use of fully amorphous polymers is also contemplated and disclosed herein.

The absorbable polymer compositions comprise physical blends of regular-to-high molecular weight polymer with a lower molecular weight counterpart of the same material as a minor component. The polymer blends are directed to semi-crystalline and fully amorphous materials. The semi-crystalline polymers have enhanced processability during extrusion, melt blowing and/or injection molding operations, due to synergistically faster crystallization kinetics. Binary blends of semi-crystalline polymers described herein have synergistically higher hydrolysis rates compared to individual components, and may provide more uniform hydrolysis characteristics throughout the polymer matrix.

The presence of lower molecular weight polymer does not affect the nucleation density of the original material, but greatly increases the growth rate of polymer spherulites. When compositions are produced from the blend of high and low molecular weight polymers disclosed herein, the rate of crystallization may be at least about 2 times faster than the rate of crystallization over an absorbable polymer made by a substantially similar polymerization process utilizing individual components. Thus, the compositions disclosed herein provide increased crystallization and/or hydrolysis rates as compared to conventional processing, as taken under the same or similar measurement conditions or techniques.

Increased crystallization, as used herein, relates to the improvement in the crystallization properties of a polymer, yielding a polymer that crystallizes at a faster rate. Crystallizing at a faster rate has advantages when melt processing the polymers disclosed herein. This is especially true when fabricating medical devices using an injection molding or fiber extrusion process. Rapid crystallization is particularly advantageous when injection molding articles from resins with low glass transition temperatures, since dimensional stability is usually achieved by crystallization. In the absence of crystallization, injection molded parts made from polymers possessing low glass transition temperatures also frequently display distortion and deformation upon removal from the mold, as they are not able to withstand the forces exerted, however mild, during the removal process.

As those skilled in the art will readily understand, as articles crystallize faster, cycle times may be decreased. Not only are there potential economic advantages resulting from the attendant decreased production costs, but faster cycle times also reduce the time the polymer resides in the machine at elevated temperatures. This reduces the amount of degradation that may occur, further improving part quality. The amount of crystallinity needed in the part prior to ejection from the mold depends on the glass transition temperature of the resin as well as the molecular weight of the resin. The lower the glass transition temperature, the higher the level of crystallinity required. It has been found that it is advantageous to have a crystallinity level of at least 10% for some synthetic absorbable polymers possessing low glass transition temperatures. In the case of fibers of higher molecular orientation, the level of crystallinity required is correspondingly higher; at least about 15% and desirably greater than about 25% may be necessary to provide dimensional stability.

Polymers contemplated for use herein include the class of polymers known as bioabsorbable polymers. These include, but are not limited to, poly(lactide), including L (−), D (+), meso and racemic lactide form, poly(glycolide), poly(dioxanone), poly(ε-caprolactone), poly(hydroxybutyrate), poly(β-hydroxybutyrate), poly(hydroxyvalerate), poly(tetramethylene carbonate), and poly(amino acids) and copolymers and terpolymers thereof. Also having utility herein are the materials selected from the group consisting of polyester amides, poly(phosphoresters)s, polyphosphazenes, poly(orthoester)s, poly(anhydride)s, anionic carbohydrate polymers, polysaccharides, poly(hydroxybutyric acid)s, polyacetals, poly(dl-lactide-co-glycolide)s, poly(l-lactide-co-glycolide)s, poly(alkylene diglycolate)s, poly(oxaester)s, poly(oxaamide)s, sulfonated aliphatic-aromatic copolyether esters, glyceride and dihydroxyacetone polymers.

In a first disclosed form, the polymer blends described herein include homogenous physical mixtures of the same polymers having two distinct molecular weight distributions, wherein a weight average molecular weight ratio of the first molecular weight distribution to the second molecular weight distribution is at least or greater than about two to one. Preferably, this ratio may be about three to one, more preferably in the range of about four to six to one. The amount of the first and the second molecular distributions is preferably in ratios to each other of between about 50/50 to about 95/5 (weight/weight) percent. More preferably, this ratio is between 70/30 and 95/5, respectively.

As indicated above, the polymeric blends disclosed herein are two component blends of a bioabsorbable polymeric material, each component selected on the basis of its weight average molecular weight distribution. The first component is selected to possess a weight average molecular weight between about 50,000 to about 2,000,000 Daltons. The second component is selected to possess a weight average molecular weight between about 10,000 to about 50,000 Daltons.

In another form, the composition comprises a two component poly(L-lactide) blend having a first component of a weight average molecular weight between about 50,000 to about 1,000,000 Daltons, preferably between about 100,000 to about 500,000 Daltons, and a second component of a weight average molecular weight between about 10,000 to about 50,000 Daltons. The first and second polymer components are blended in a ratio between about 60/40 to 80/20 (weight/weight) percent, respectively. The rate of crystallization of the composition is at least about two times or greater than the rate of crystallization exhibited by either the first or second polymer component alone, when evaluated using isothermal crystallization over a temperature range of between about 85° C. to about 150° C. The composition is capable of crystallizing in the range of between about 140° C. to about 150° C., as verified by calorimetric measurements. Similarly, the rate of hydrolysis of the composition, measured in distilled water at a constant pH value is at least about three times or greater than the rate of hydrolysis exhibited by either the first or second polymer component alone, as evaluated using an absorption profiler instrument.

In another form, the composition comprises a two component poly(p-dioxanone) blend having a first polymer component with a weight average molecular weight between about 50,000 to about 100,000 Daltons, and a second polymer component with a weight average molecular weight between about 10,000 to about 30,000 Daltons. The first and second components are blended in ratios with respect to each other of between about 60/40 to 95/5 (weight/weight) percent, respectively. The rate of crystallization of the blended composition is substantially greater than the rate of crystallization exhibited when utilizing either the first or second polymer component alone, when evaluated using isothermal crystallization over a temperature range of between about 40° C. to about 80° C. Moreover, the rate of crystallization of the blended composition is at least about three times or greater than the rate of crystallization exhibited when utilizing either the first or second polymer component alone, when evaluated over the temperature range between about 70° C. to about 80° C. The blended polymer composition can be crystallized at the isothermal temperature of about 80° C., as verified by means of calorimetric measurements. Similarly, the rate of hydrolysis of the composition, measured in distilled water at a constant pH value is substantially greater than the rate of hydrolysis exhibited by either the first or second polymer component alone, as evaluated using an absorption profiler instrument.

In accordance herewith, a medical device may be produced from a blended absorbable polymeric composition disclosed herein exhibits substantially increased rates of hydrolysis and/or crystallization, as compared to the rate of hydrolysis and/or crystallization of a device produced from an individual polymeric component of the blended composition. The medical devices contemplated herein include those selected from the group consisting of sutures, clips, staples, pins, screws, fibers, stents, gel caps, tablets, microspheres, meshes, clamps, plates, hooks, buttons, snaps, prosthetics, grafts, injectable polymers, vertebrae discs, anchoring devices, suture anchors, septal occlusion devices, injectable defect fillers, preformed defect fillers, bone waxes, cartilage replacements, spinal fixation devices, drug delivery devices, foams and films.

The blended compositions disclosed herein may further comprise an active medical ingredient substantially homogenously mixed with a polymer or copolymer blend of the present invention. It is envisioned that the active medical ingredient may be released in a living body organism by diffusion and/or a polymer hydrolysis mechanism.

In one form, provided is a composition comprising a drug delivery carrier comprising a first amount of a fully amorphous bioabsorbable polymer having a first hydrolysis rate and a first molecular weight distribution; and a second amount of said fully amorphous bioabsorbable polymer having a second hydrolysis rate and a second molecular weight distribution having a weight average molecular weight between about 10,000 to about 50,000 Daltons, the weight average molecular weight ratio of said first molecular weight distribution to said second molecular weight distribution is at least about two to one; and a pharmaceutically active agent, wherein a substantially homogeneous blend of said first and second amounts of said fully amorphous bioabsorbable polymer is formed in a ratio of between about 50/50 to about 95/5 weight/weight percent, said substantially homogeneous blend having a hydrolysis rate greater than each of said first hydrolysis rate and said second hydrolysis rate. In one form, the pharmaceutically active agent may be selected from the group consisting of analgesics, anti-inflammatory compounds, muscle relaxants, anti-depressants, anti-viral, antibiotic, anesthetic, and cytostatic compounds. In another form, the analgesics may include acetaminophen or ibuprofen. In yet another form. the anti-inflammatory compounds include compounds selected from the group consisting of non-steroidal anti-inflammatory drugs (NSAIDs), prostaglandins, choline magnesium salicylate, salicyclic acid, corticosteroids, methylprednisone, prednisone, and cortisone.

The method of making the bimodal compositions disclosed herein may, in general, comprise a step of blending a first component having a first molecular weight distribution with a second component having a second molecular weight distribution. In one form, the blending step is performed by melting the amounts of first and second components in a sufficient quantity at a temperature above the melting point of the highest melting component, so as to ensure forming a substantially homogenous mixture. In another form, the blending step is performed by dissolving the amounts of first and second molecular weight distributions in a sufficient quantity in a suitable solvent, and subsequently, removing the solvent, thereby forming a substantially homogenous mixture. The dissolving step of the method may further comprise selecting a suitable solvent from the group consisting of acetone, ethyl acetate, ethyl lactide, tetraglycol, chloroform, tetrahydrofuran, dimethyl sulfoxide, N-methylpyrollidinone, dibutyl phthalate, methylene chloride, methyl ethyl ketone, dibasic esters, methyl isobutyl ketone, dipropylene glycol, dichloromethane and hexafluoroisopropyl alcohol.

Figure 12:
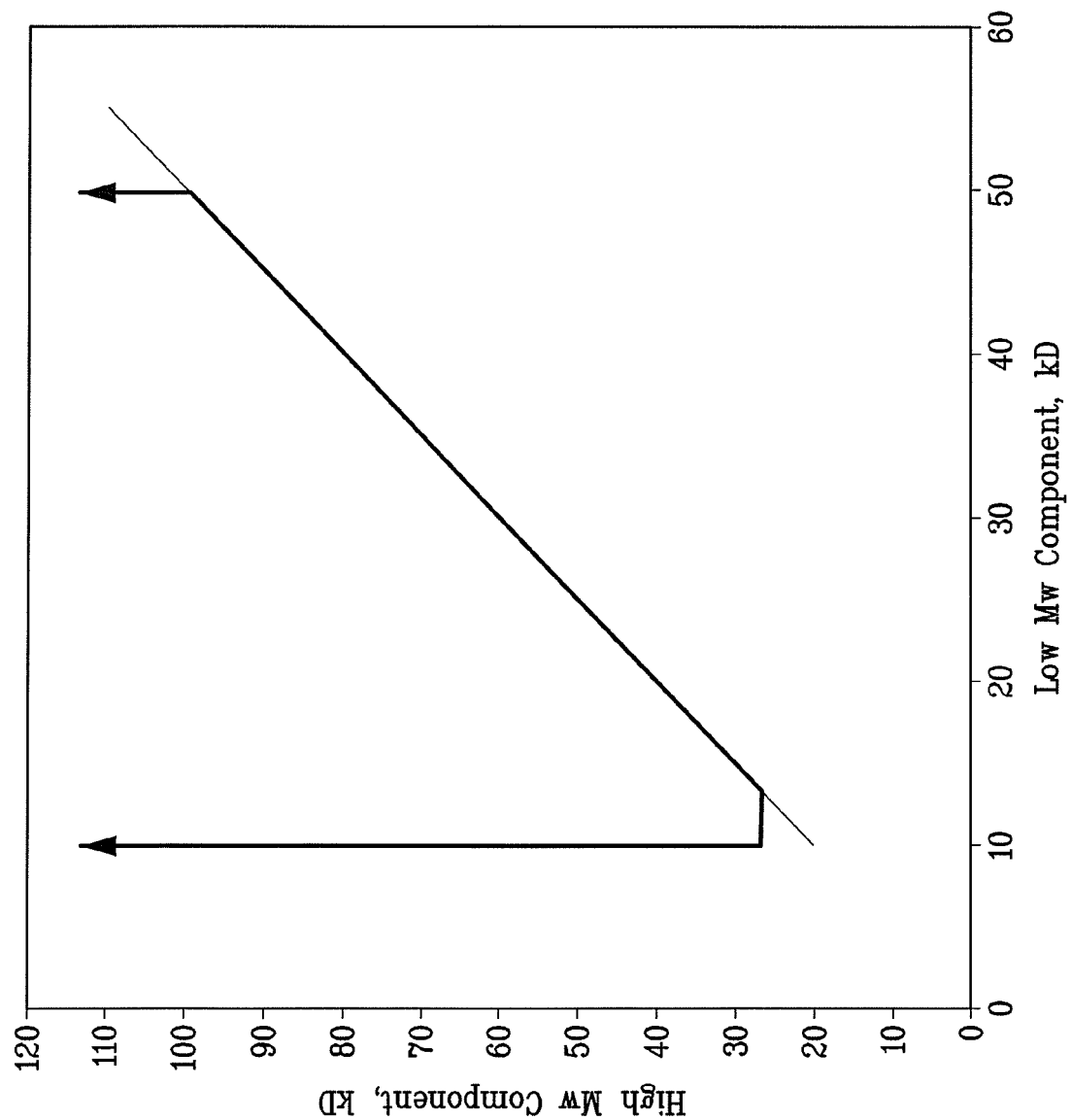
FIG. 12 presents ranges of molecular weights for certain bimodal polymeric blends disclosed herein.

In one form, a useful nonwoven fabric may be produced by a melt blown process using PDS with an intrinsic viscosity (IV) of about 0.8 dL/g. As may be appreciated by those skilled in the art, this corresponds to a Mw of about 29,000 Daltons. In one form, the molecular weight range of the lower molecular component may be from about 10,000 Daltons to 50,000 Daltons, while the higher molecular weight polymer component is at least two times the molecular weight of the lower molecular weight component. Additionally, in one form, the higher molecular weight component may have a molecular weight of at least 25,000 Daltons. The molecular weight range is further depicted in FIG. 12:

In accordance with this disclosure a detailed description of a melt blown nonwoven process will now be described. A typical system for use in a melt blown nonwoven process consists of the following elements: an extruder, a transfer line, a die assembly, a web formation system, and a winding system.

As is well known to those skilled in the art, an extruder consists of a heated barrel with a rotating screw positioned within the barrel. The main function of the extruder is to melt the polymer pellets or granules and feed them to the next element. The forward movement of the pellets in the extruder is along the hot walls of the barrel between the flights of the screw. The melting of the pellets in the extruder results from the heat and friction of the viscous flow and the mechanical action between the screw and the walls of the barrel. The transfer line will move molten polymer toward the die assembly. The transfer line may include a metering pump in some designs. The metering pump may be a positive-displacement, constant-volume device for uniform melt delivery to the die assembly.

As may be appreciated, the die assembly is a critical element of the melt blown process. It has three distinct components: a polymer-feed distribution system, spinnerretts (capillary holes), and an air distribution system. The polymer-feed distribution introduces the molten polymer from the transfer line to distribution channels/plates to feed each individual capillary hole uniformly and is thermal controlled. From the feed distribution channel the polymer melt goes directly to the die capillary. The polymer melt is extruded from these holes to form filament strands which are subsequently attenuated by hot air to form fine fibers. During processing, the entire die assembly is heated section-wise using external heaters to attain the desired processing temperatures. The air distribution system supplies the high velocity hot air. The high velocity air is generated using an air compressor. The compressed air is passed through a heat exchange unit, such as an electrical or gas heated furnace, to heat the air to desired processing temperatures.

As soon as the molten polymer is extruded from the die holes, high velocity hot air streams attenuate the polymer streams to form microfibers. As the hot air stream containing the microfibers progresses toward the collector screen, it draws in a large amount of surrounding air that cools and solidifies the fibers. The solidified fibers subsequently get laid randomly onto the collecting screen, forming a self-bonded nonwoven web. The collector speed and the collector distance from the die nosepiece can be varied to produce a variety of melt-blown webs. Typically, a vacuum is applied to the inside of the collector screen to withdraw the hot air and enhance the fiber laying process.

The melt-blown web is typically wound onto a tubular core and may be processed further according to the end-use requirement.

Specific embodiments of the present invention will now be described further, by way of example. While the following examples demonstrate certain embodiments of the invention, they are not to be interpreted as limiting the scope of the invention, but rather as contributing to a complete description of the invention.

EXAMPLES

Several commercially available instruments were utilized. A description of the equipment used follows.
Differential Scanning Calorimetry (DSC)

Overall crystallization rates depend principally on two factors: the concentration of growing spherulites over time (nucleation rate) and the rate of spherulitic growth. As expected, these processes have a measurable effect on calorimetric data. Calorimetric results were generated on a TA Instruments Differential Scanning calorimeter, Model 2910 MDSC, using dry $N_2$ as a purge gas.

Crystallization studies were conducted in the following manner: after melting, the sample is rapidly cooled to a temperature of interest and the crystallization measured under the controlled isothermal conditions. Isothermal melt crystallizations of the absorbable polymers were conducted as follows: a sample of about 4-5 mg was first melted and maintained for five minutes at temperatures of about 30-40° C. above the melting point of the polymer to remove any nucleation sites present in a sample. Test materials were rapidly cooled down (ca. 35° C./min) to the constant test (crystallization) temperature. The isothermal method assumes that no crystallization occurs before the sample reaches the test temperature. In each case, crystallization behavior was characterized over a wide range of temperatures. Calorimetric runs were made in randomized order to avoid any bias due to possible molecular weight degradation. All temperature runs for a given polymer were performed on a single sample. As may be appreciated, the self-consistency of the data engenders confidence that molecular weight loss during testing is not of a concern.

The widely excepted parameter to express the overall crystallization rate is the crystallization half-time, $t_{1/2}$. This is the time needed for crystallinity to reach 50% conversion.
Hot-Stage Optical Microscopy (HSOM)

Optical hot stage experiments were conducted using a Mettler FP90 central processor with a Mettler FP82HT hot stage to control sample conditions. The hot stage, with nitrogen flow, was mounted on a Nikon SMZ-U microscope utilizing linear polarized light. The instrument is equipped with 1× objective, a set of cross-polarizers and a 1:10 zoom. Images from the microscope were obtained using a Microimage i308 Low Light Integrating Video Camera. The digital images were captured and analyzed using Image Pro Plus (Version 4.0) imaging software.

Growth rate measurements at each temperature were conducted on freshly prepared films to avoid possible degradation problems that might arise with these hydrolytically unstable polyesters. A small amount of ground polymer was placed on the microscope glass slide and a thin cover glass positioned on top of it. The resulting sandwich was then inserted into a hot stage block regulated at temperatures between about 30-40° C. above the melting point. The polymeric sample was then melted for five minutes under a nitrogen purge. A thin film was obtained by applying a slight pressure on the top of cover glass. Monitoring with a digital micrometer, the polymer thickness was adjusted to 0.135 mm for each sample run.
Wide Angle X-ray Diffraction (WAXD)

Additional supporting evidence was obtained by conventional X-Ray analysis. The WAXD measurements of the isothermally grown films were carried out on a Siemens Hi-Star™ unit using CuKα radiation at the wavelength of 1.542 Å. The instrument was operated at 40 kV and 40 mA with the collimator size of Ø0.5 mm. The convolution of the X-ray images and the calculation of crystallinity content were conducted using DIFFRAC PLUS™ software developed by Siemens.

Example 1

Crystallization Kinetics of PLLA Homopolymers as a Function of Different Molecular Weights A series of PLLA homopolymers having substantially different molecular weights were examined calorimetrically. Weight average molecular weights are: 50,000 g/mol (50 k), 100,000 (100 k), 300,000 (300 k), 700,000 (700 k). The high molecular weight sample, identified as Test Sample 1, has an inherent viscosity of 7.5 g/dL, but the exact weight average molecular weight was difficult to determine. Calorimetric evaluation (by DSC) of PLLA samples after quenching from the melt, using the heating rate of 10° C./min revealed glass transition temperatures in the range from 60 (for the lowest molecular weight material) to 64° C. (for the highest molecular weight material), and melting temperatures from 177.0 (for the lowest molecular weight material) to 183.5° C. (for the highest molecular weight material). Overall crystallinity for PLLA homopolymers, as determined by WAXD, is between 40 and 50%.

Crystallization properties for the aforementioned polymers were evaluated next under a variety of isothermal conditions utilizing DSC equipment. It was discovered that the high molecular weight polymer used in this study, Test Sample 1, made by solid-state (low temperature) polymerization, exhibited faster crystallization kinetics than other low molecular counterparts. This is demonstrated in FIG. 1, where the crystallization rates ($t_{1/2}$) for this polymer were compared to the kinetics of the lower molecular weight PLLA samples (50 k, 100 k, and 300 k). It was initially expected that, due to the presence of long, hardly mobile chains of Test Sample 1 polymer, the crystallization rate for this sample would be the slowest at any given crystallization temperature. Instead, this polymer demonstrated the fastest overall crystallization kinetics, when compared to all samples evaluated. This difference in crystallization rate is exceptionally large in the higher temperature range from 120 to 150° C.

Since crystallization is composed of nucleation and crystal growth, polarized optical microscopy was used to differentiate the contributions of these two processes to the overall crystallization rate. Using HSOM technique it was found that the polymer Test Sample 1 exhibits similar nucleation density when compared with other samples in the PLLA series. However, Test Sample 1 polymer exhibited the fastest spherulitic growth rate, 7.9 μm/min (measured at 130° C.), among other counterparts at any given crystallization temperature. For comparison, a lower molecular weight polymer, 100 k was found to have slower spherulitic growth, 6.4 μm/min (at 130° C.).

Figure 2:
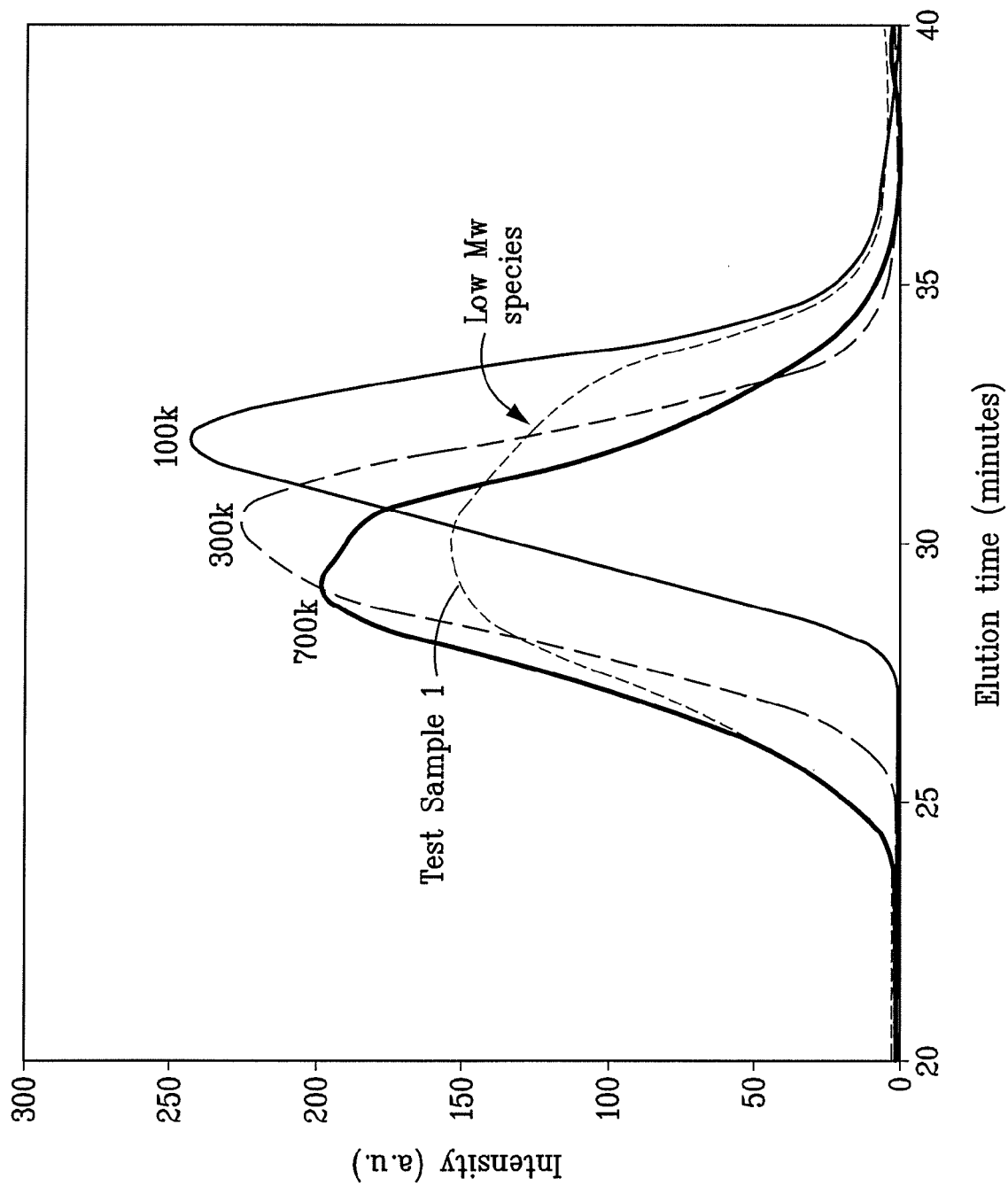
FIG. 2 presents GPC molecular weight distribution curves for several PLLA homopolymers.

Further investigation of the polymer Test Sample 1 by GPC measurements revealed that this material has a bimodal molecular weight distribution. GPC curves of different PLLA samples are shown in FIG. 2. As may be seen, the bimodal molecular weight distribution for Test Sample 1 sample is clearly evident. One possible explanation of the bimodal molecular weight distribution in PLLA could be the presence of partial degradation processes generated from the variability in distribution of crystalline and amorphous regions within the sample. These variations might be associated with the inherent nature of the solid-state (low temperature) polymerization used to make this polymer.

Figure 3:
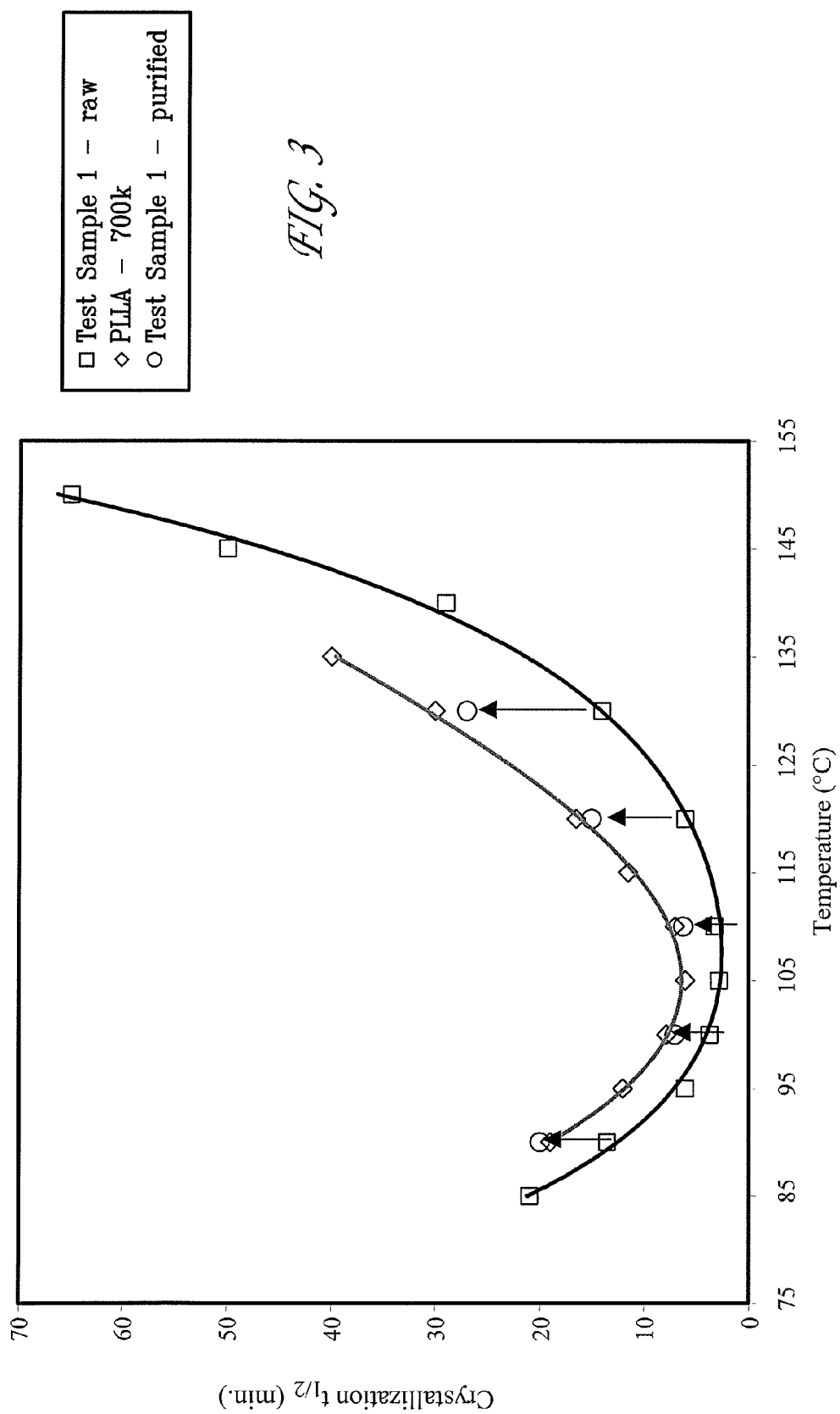
FIG. 3 presents DSC crystallization kinetics for a Test Sample 1 polymer before and after purification, as a function of crystallization temperature. Data for PLLA homopolymer 700 k are added for comparison.

In order to remove the lower molecular weight fraction, the polymer was extracted by acetone. The purified polymer was re-measured by GPC and only a single peak molecular weight distribution was found, confirming the substantial removal of the shorter chain population. The next step was to reexamine the crystallization kinetics of the purified Test Sample 1 sample. It was found that the crystallization rate of the purified Test Sample 1 polymer was considerably reduced, as shown in FIG. 3. At any given crystallization temperature, the fractionated polymer Test Sample 1 exhibits virtually the same crystallization rate as the high molecular weight PLLA-700 k polymer. This was a strong indication that the low molecular weight fraction was responsible for the enhanced crystallization kinetics.

Example 2

Crystallization Kinetics of PLLA Blends Exhibiting Enhanced Crystallization Rates This example presents crystallization results for specifically designed blends of the higher molecular weight PLLA sample (Mw=300,000 g/mol, 300 k) and lower molecular weight PLLA (Mw=50,000 g/mol, 50 k), in the percent weight ratios of 300 k/50 k for 80/20, 70/30, and 60/40. In general, lower molecular weight polymers are expected to crystallize faster than their higher molecular weight counterparts due to the higher mobility of their macromolecular chains in the melt phase accompanied by lesser entanglement effects. However, it was discovered that the blending of high molecular weight PLLA with its lower molecular weight counterpart resulted in much higher crystallization rates for the polymer blends examined under a wide range isothermal conditions. At the same time, important physical properties such as the glass transition temperature ($T_g$ around 63° C.) and the melting point characteristics ($T_m$ around 182° C.) were found to be in the expected range; these values being directly related to the concentration of individual components in the prepared formulations. As may be appreciated, this feature allows for fine-tuning of desired final mechanical properties of the original higher molecular weight material.

Figure 4:
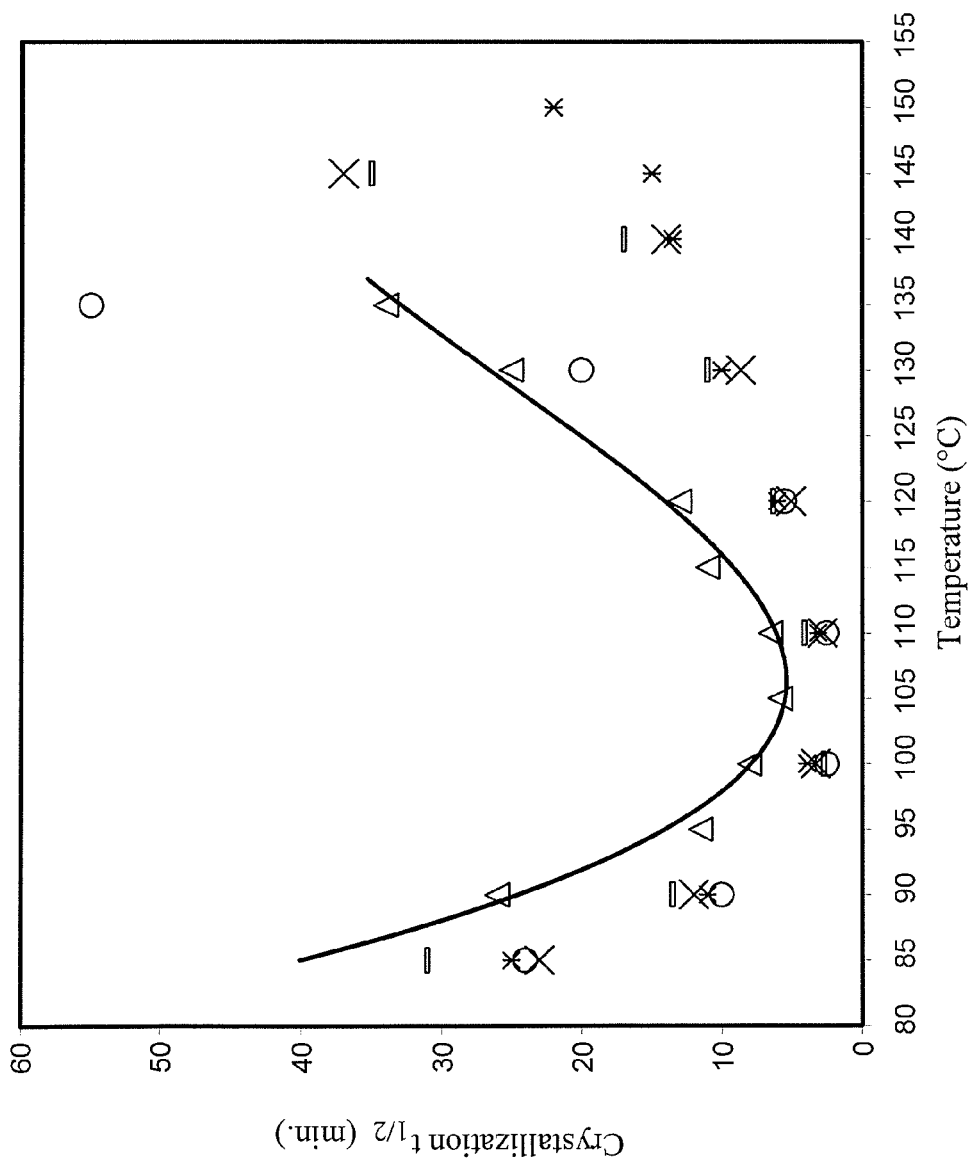
FIG. 4 presents DSC crystallization kinetics for two PLLA homopolymers (300 k and 50 k), and a variety of blends thereof, as a function of crystallization temperature.

Referring to FIG. 4, blend compositions, of the type disclosed herein, crystallized much faster than the 300 k polymer at any given crystallization temperature. At very low temperatures, where the 300 k polymer could not readily crystallize (e.g. 85° C. or below), it was found that, for all blends, crystallization did occur, demonstrating the strong capability for nucleation and growth. At the intermediate temperature range, using the same set of conditions, blends rich in the 300 k polymer exhibited approximately the same crystallization kinetics as a 50 k monodisperse polymer, significantly faster than those obtained for the 300 k material. However, at temperatures higher than 120° C., data show dramatically faster rates for blends compared to both monodisperse samples (300 k & 50 k). Intuitively, it would be expected that the data would fall in the range between those generated on neat samples. Furthermore, at temperatures higher than 135° C., two monodisperse samples (300 k & 50 k) cannot crystallize to the calorimetrically measurable level, while the blends, examined in the same temperature zone, exhibit relatively fast kinetics. The 70/30 blend composition was found to be particularly effective, undergoing measurable crystallization trends even at temperatures as high as 150° C. This may be very useful in certain processing conditions where, for instance, relatively low melt viscosity is required, followed by on-line crystallization that can ultimately improve the dimensional stability of the product.

Example 3

Melt Index Calculation for PLLA Polymers at 235° C. Using Standard 3700 g Weight Melt index, MI measurements were conducted on 50 k and 300 k monodisperse samples, as well as on various blends thereof, to investigate the effect of the addition of low molecular weight component on the melt viscosity. These data are presented in Table 1.

TABLE 1

Melt Index of Selected PLLA Homopolymers and Blends

| Polymer | Melt Index, MI (g) Standard wt. 3,700 g | Melt Index, MI (g) wt. 6,600 g | Comments |
|---|---|---|---|
| 300k | / | 0.2523 | No flow induced using the standard weight. |
| 50k | / | / | Flow was too fast using the standard weight - not enough material to measure MI. |
| 300k/50k 80/20 | 0.0219 | / | / |
| 300k/50k 70/30 | 0.0374 | / | / |
| 300k/50k 60/40 | 0.0596 | / | / |

Instrument: Tinius Olsen Extrusion Plastometer with MP987 Controller, Willow Grove, Pa.

Results from Table 1 demonstrate that, in addition to increasing the crystallizability of the polymers, blending improves the melt processability of high molecular weight polymers. The melt index of the blends systematically increased with an increase in the concentration of the low molecular weight component. This finding is very important for the case of a very high molecular weight polymer that may not otherwise be melt processed due to low mobility and high macromolecular chain entanglement.

Example 4

PDS Compositions Having Enhanced Crystallization Rates

In order to demonstrate that the crystallization kinetics of poly(dioxanone) (PDS) can be improved by the methods disclosed herein, a set of varied weight average molecular weight polymers was employed (80,000 g/mol—80 k, and a lower molecular weight counterparts 24,000 g/mol—24 k) to produce an 80 k/24 k 70/30 wt. % blend. The blends were made by mixing the homopolymers in the melt without using a solvent. Calorimetric data on the monodisperse samples and a blend, subjected to an annealing step at 60° C. for 3 hours, using the heating rate of 10° C./min, produced glass transition temperatures of −15.5° C. for the 24 k polymer, −11.5° C. for the 80 k polymer, and −12.5° C. for the 70/30 blend. Melting points are 103.5° C. for the 24 k polymer, 108.5° C. for the 80 k polymer, and 106.0° C. for the 70/30 blend, while overall crystallinity extents are 45% for low molecular weight polymers and 39-40% for regular molecular weight PDS and their 70/30 blend.

Figure 5:
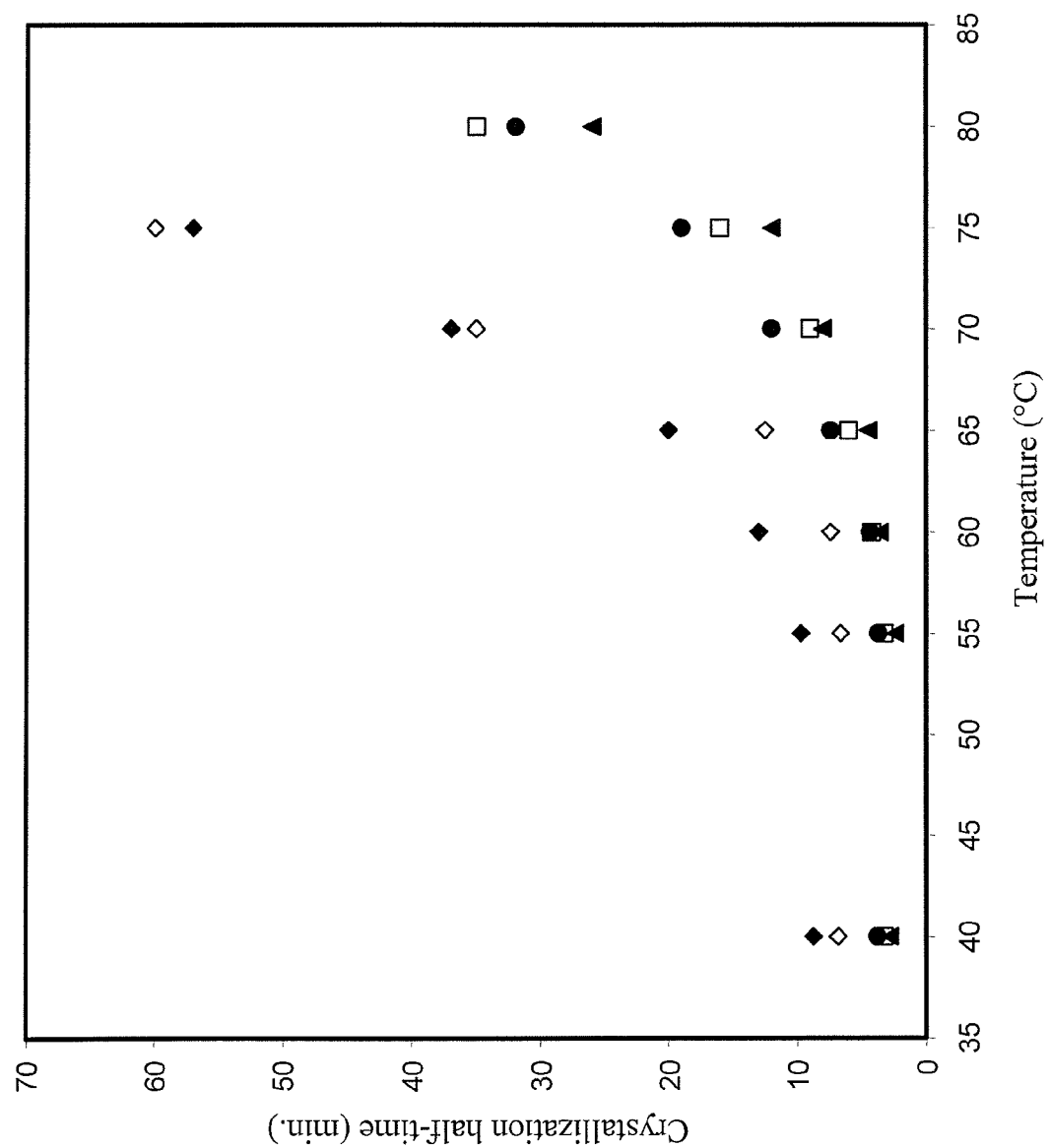
FIG. 5 presents DSC crystallization kinetics for two PDS homopolymers (80 k and 24 k) and three blend compositions thereof, as a function of crystallization temperature.

Isothermal crystallization measurements were performed next, using the DSC crystallization procedure described earlier in the text. As shown in FIG. 5, similar to PLLA case, it was found that 60/40, 70/30 and 80/20 PDS blends crystallize significantly faster than the monodisperse PDS components (80 k and 24 k) alone. Crystallization rates dramatically improved in each temperature regime studied. Furthermore, at the highest temperature zone (80° C.), both monodisperse samples showed no crystallization pattern by DSC; on the other hand, using the same conditions, crystallization was detected and the rate was calculated for 60/40, 70/30 and 80/20 PDS blend.

Example 5

Effect of Different PDS Blend Compositions on Isothermal and Non-isothermal Crystallization Rates This example presents crystallization and mechanical properties of PDS homopolymers 80 k and 24 k, and their 95/5 and 90/10 blends. The glass transition temperature and melting characteristics of the 95/5 and 90/10 blends are nearly identical to the 80 k PDS reported earlier in the text.

Figure 6:
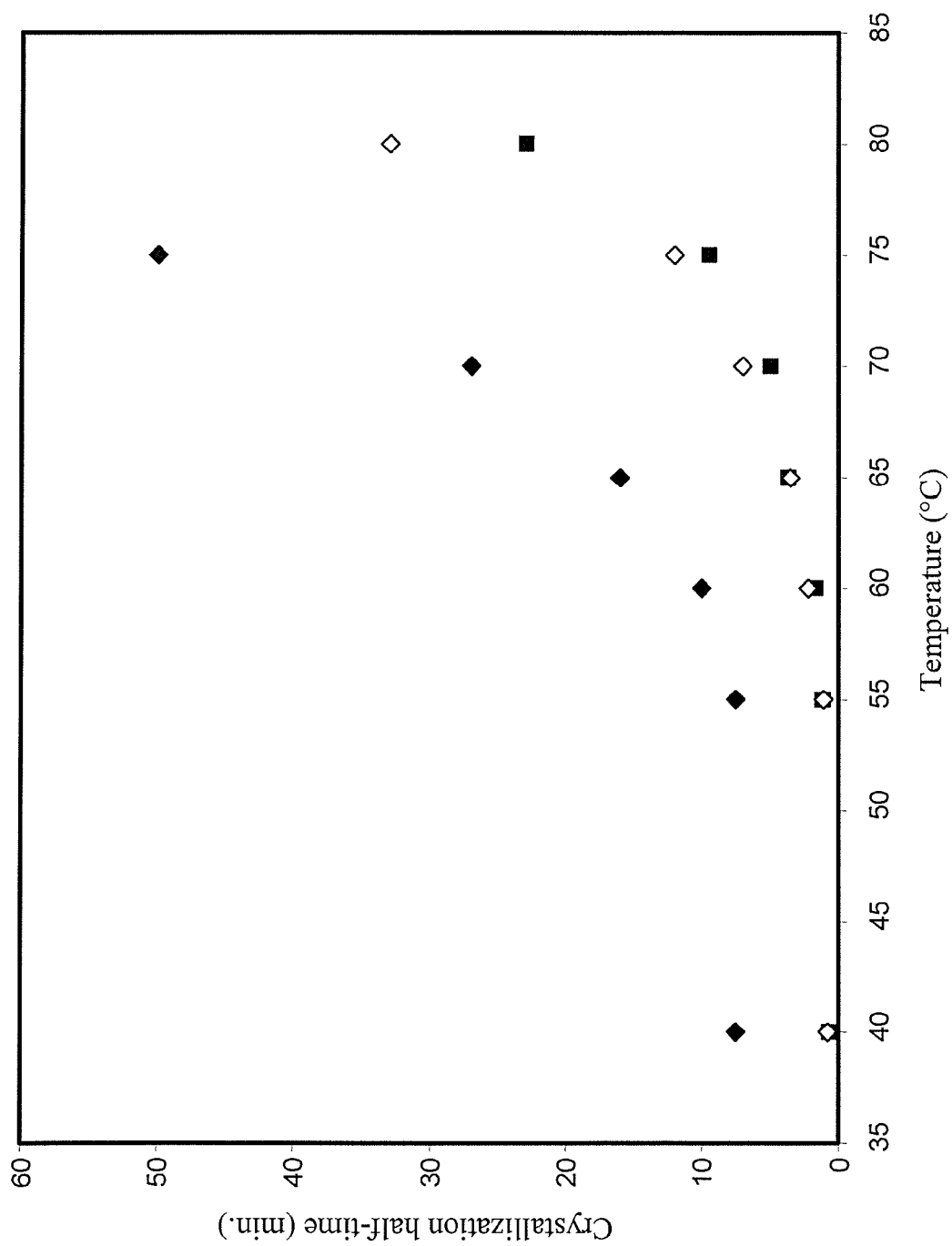
FIG. 6 presents DSC isothermal crystallization kinetics for an 80 k PDS homopolymer and two blend compositions, as a function of crystallization temperature.

Isothermal crystallization data of these blend formulations were examined first. Again, the data showed a dramatic increase in crystallization rates for the two blends, as compared with PDS having regular and lower molecular weight chains. FIG. 6 presents results obtained for an 80 k PDS polymer and two of blends containing a very low concentration of a 24 k PDS polymer component. Only 5% of low molecular weight polymer appears to be necessary to produce a beneficial effect on the crystallization rate of a PDS homopolymer. This would be expected to be very important in fiber extrusion applications where the mechanical strength associated with higher molecular weight material must be preserved.

Figure 7:
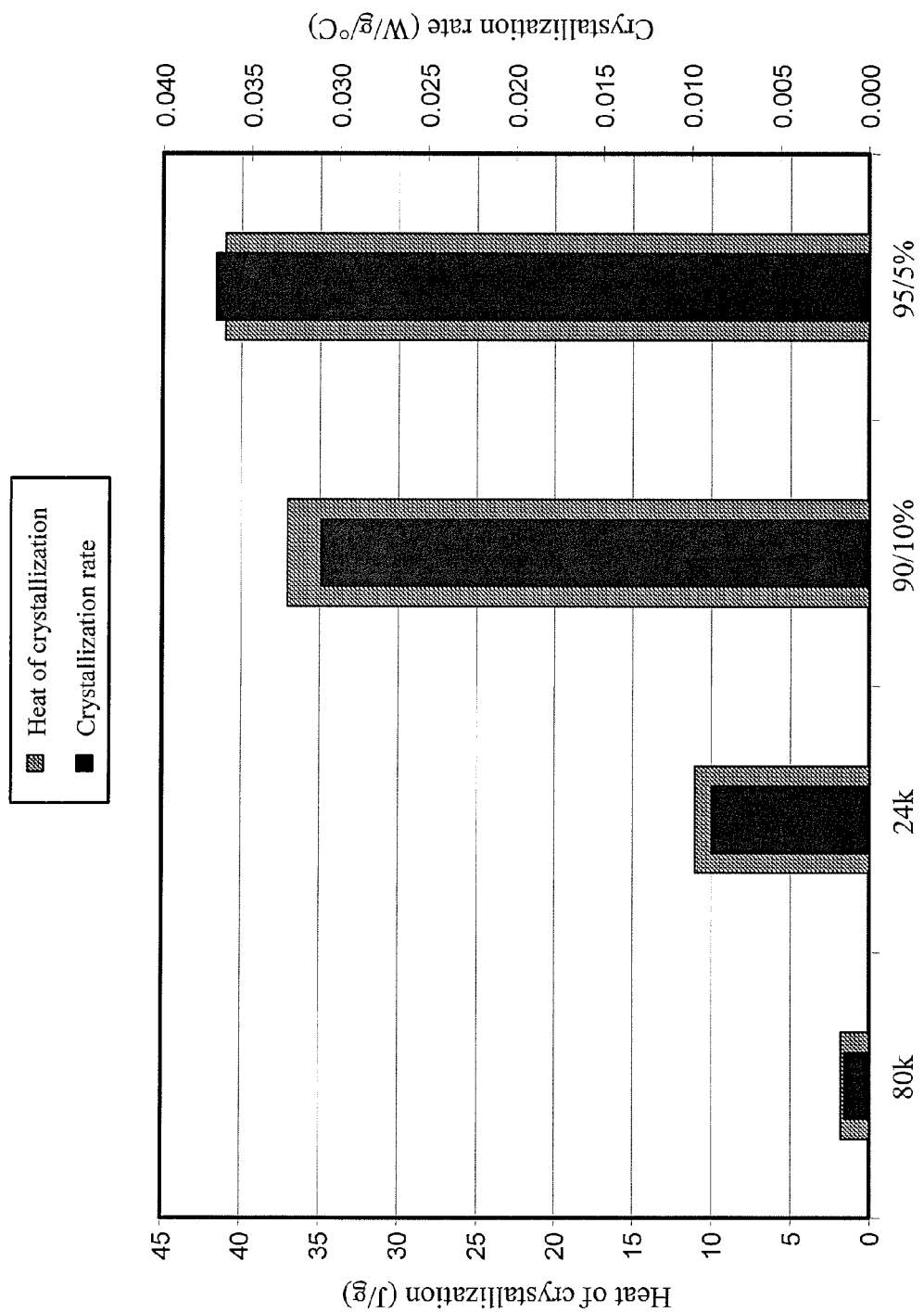
FIG. 7 presents DSC non-isothermal crystallization kinetics for an 80 k PDS homopolymer and two blend compositions, during the cooling from the melt at a constant cooling rate of 10° C./min.

Non-isothermal DSC crystallization data were obtained for several PDS polymers during cooling from the melt at a constant cooling rate of 10° C./min. Again, a dramatic increase in crystallization rates was observed for the two blends compared to both PDS homopolymers using this non-isothermal method. As shown in FIG. 7, values for the enthalpy (heat) of crystallization, $\Delta H_C$, developed during the cooling step, as well as the crystallization rate (obtained from the initial slope of the crystallization peak) for 90/10 and 95/5 blends are higher than the corresponding values for 80 k and 24 k PDS homopolymers.

Example 6

Effect of Different PDS Blend Compositions on Mechanical Tensile Strength Properties Selected mechanical properties of regular molecular weight PDS film and three blends 95/5, 90/10, and 80/20 were examined using an Instron Tensile testing machine to determine the effect of the addition of low molecular weight PDS component on the mechanical properties of films prepared from studied materials. These data are summarized in Table 2, below.

TABLE 2

Selected Mechanical Properties of PDS Films

| Polymer | Load at Peak (lbf) | % Strain at Peak | Displacement at break (in) | Young's Modulus (ksi) |
|---|---|---|---|---|
| Regular PDS, 80k | 14.0 | 1056 | 5.3 | 48 |
| 80/20 blend | 12.5 | 1250 | 6.3 | 43 |
| 90/10 blend | 13.0 | 1211 | 6.1 | 40 |
| 95/5 blend | 13.5 | 1125 | 5.7 | 45 |

The mechanical results in Table 2 suggest that only a minimal effect on the mechanical properties for the three blends was detected when compared to the properties of the 80 k unblended material. Moreover, in the case of the 95/5 blend, the effect was substantially negligible. This represents an important discovery that suggests that the blending of relatively small amount of lower molecular weight polymer does not diminish the final physical properties of a product.

Example 7

Enhanced Absorption Rates for PLLA Blends

The hydrolysis profile method determines the hydrolytic degradation time of ester-containing samples. The hydrolysis profile is generated by first hydrolytically degrading a test specimen, while maintaining a constant pH by titrating with a standard base and measuring the quantity of base used with time. This measurement and titration procedure is automated through the use of a pH stat instrument (718 STAT Titrator Complete, by MetroOhm, using Software TiNet 2.4). The samples are placed in a 70 mL stirred, sealed, bath of deionized water held at 75° C.+/−0.2° C. and at a pH of 7.27. Each sample bath is continuously monitored for pH changes (drops in pH) from the set point of 7.27. If any decrease is measured, a sodium hydroxide solution is added to return to the bath 7.27 (NaOH 0.05N). The following measurements are recorded by computer: temperature, volume of base added (V(t)), and pH, over time. The V(t) time-course is analyzed to yield the time to 50% hydrolysis, t 50. Prior to each sample run, the pH probe at each test station is calibrated at pH values of 4.0, 7.0 and 10.0, using standard solutions.

Figure 8:
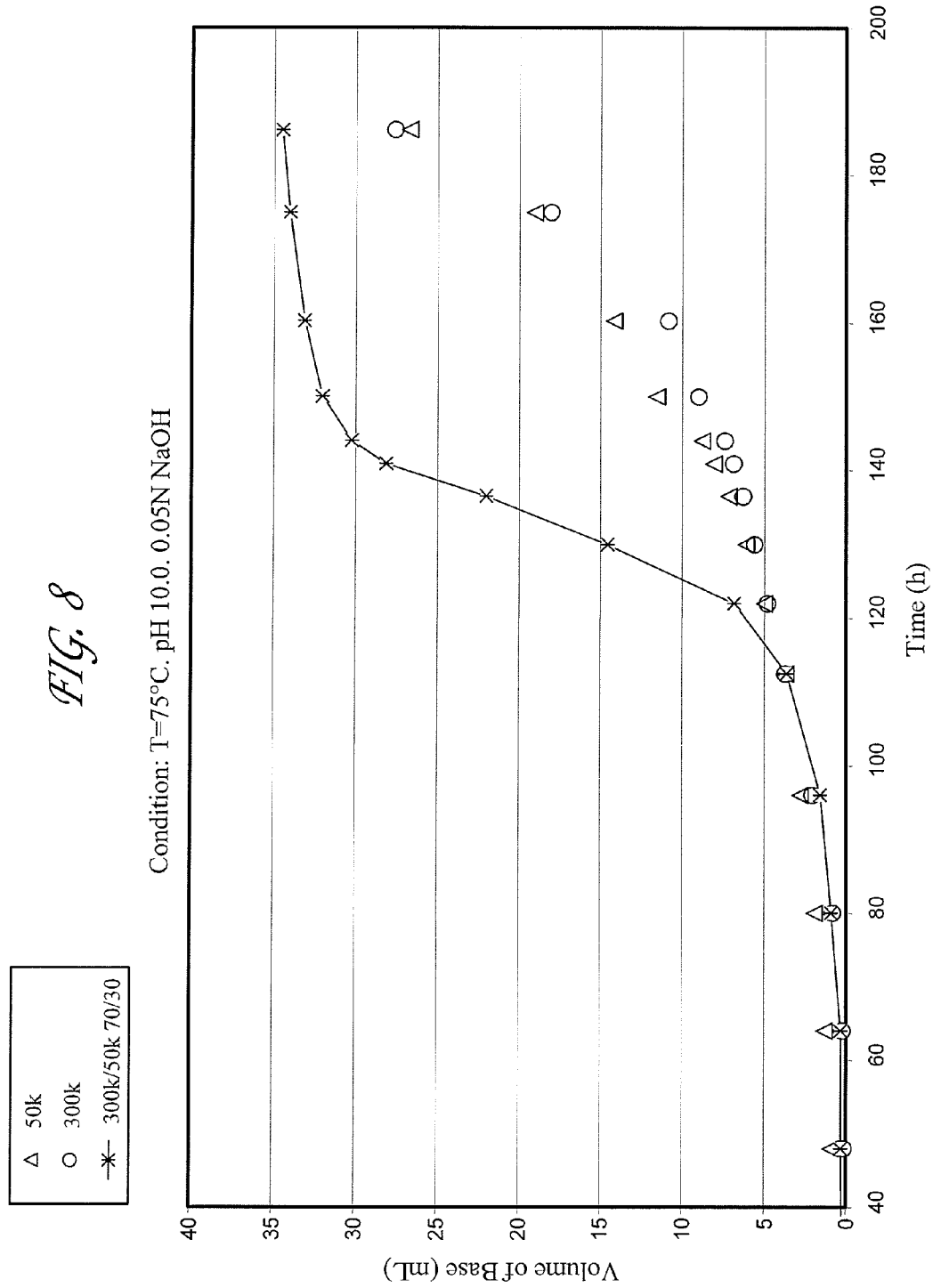
FIG. 8 presents hydrolysis profiles for two PLLA homopolymers (300 k and 50 k) and a 70/30 blend thereof.

Hydrolysis measurements of PLLA samples were conducted using the automated hydrolysis profile at 75° C., a constant pH value of 10.0 and a sodium hydroxide solution (0.05N) as a base. Prior to the experiments all samples were annealed using the same temperature condition, namely, 100° C. for 12 hours. Hydrolysis data obtained on solvent cast films made from PLLA homopolymers, 300 k, 50 k and their 70/30 wt. % blend are shown in FIG. 8. A faster absorption rate for the 70/30 blend was observed over the individual components alone. A direct comparison of kinetic parameters, including comparing the time at which 50% of the polymer hydrolyzed, suggests that the hydrolysis rate for the 70/30 blend was three or more times faster than that observed for the individual components, alone. It would be expected that the hydrolysis rate value of the blend should reside in between the rates observed for the 300 k and 50 k samples. This, in addition to the potential uses in the medical device and drug delivery sectors, may additionally provide a beneficial impact on the waste disposal issues for PLLA based polymers when used as packaging materials.

Figure 9:
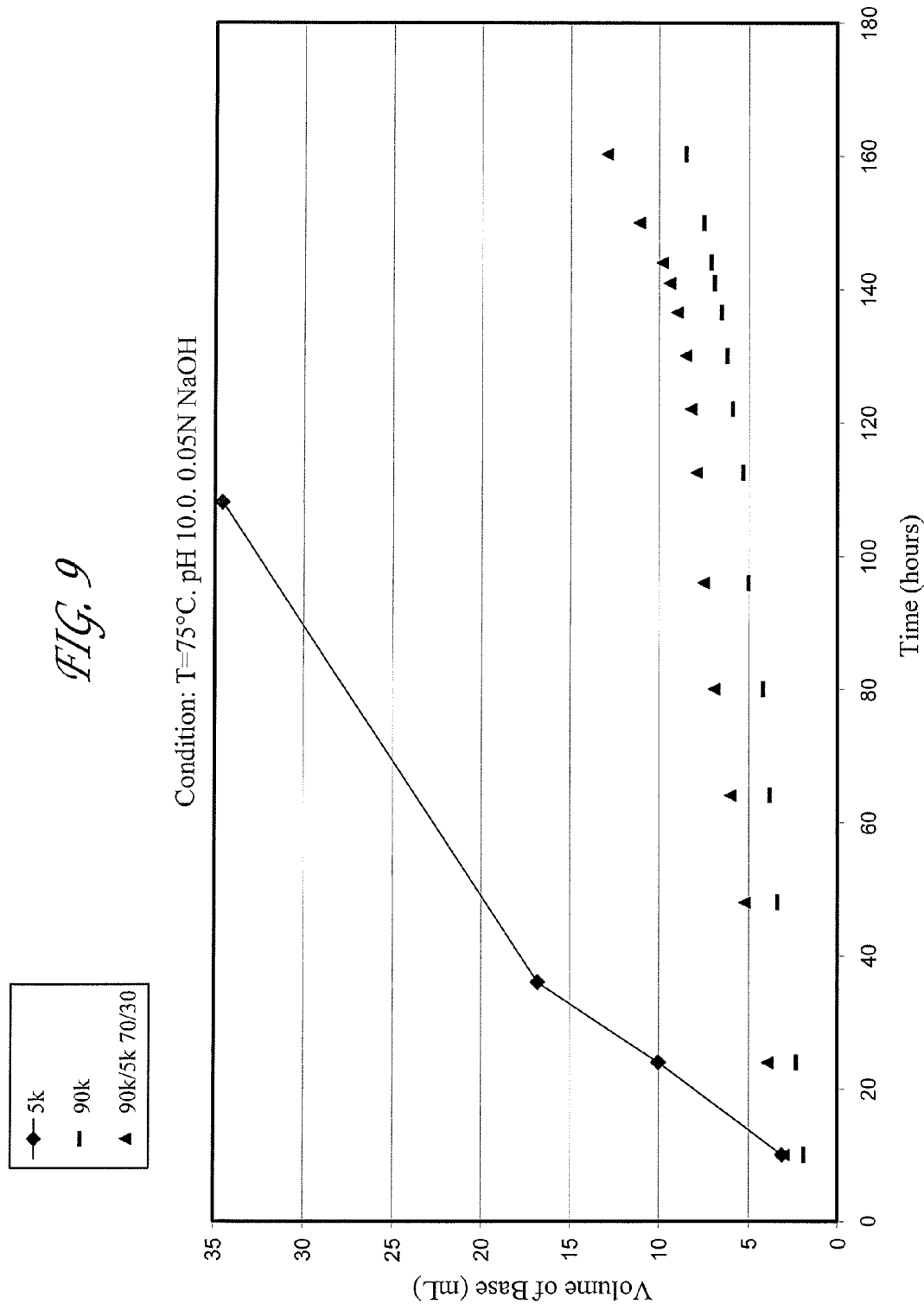
FIG. 9 presents hydrolysis profiles of two PDS homopolymers (90 k and 5 k) and their 70/30 blend for comparative purposes.

For comparative purposes, FIG. 9 presents the hydrolysis profiles obtained for solvent cast films made from both 5,000 Dalton and 90,000 Dalton PLLA homopolymers, and a 70/30 wt. % blend of 90,000 to 5,000 homopolymer. As may be appreciated, the 5,000 Dalton PLLA homopolymer is well below the weight average molecular weight range of about 10,000 to about 50,000 Daltons and, as would be expected, the data presented in FIG. 9 fails to exhibit the benefits of the blends produced in accordance herewith.

Example 8

Enhanced Absorption Rates of Various PDS Polymers and Blends

Example 8 examines a wider range of PDS blend compositions, including 95/5, 90/10, 80/20 and 70/30 blends.

Figure 10:
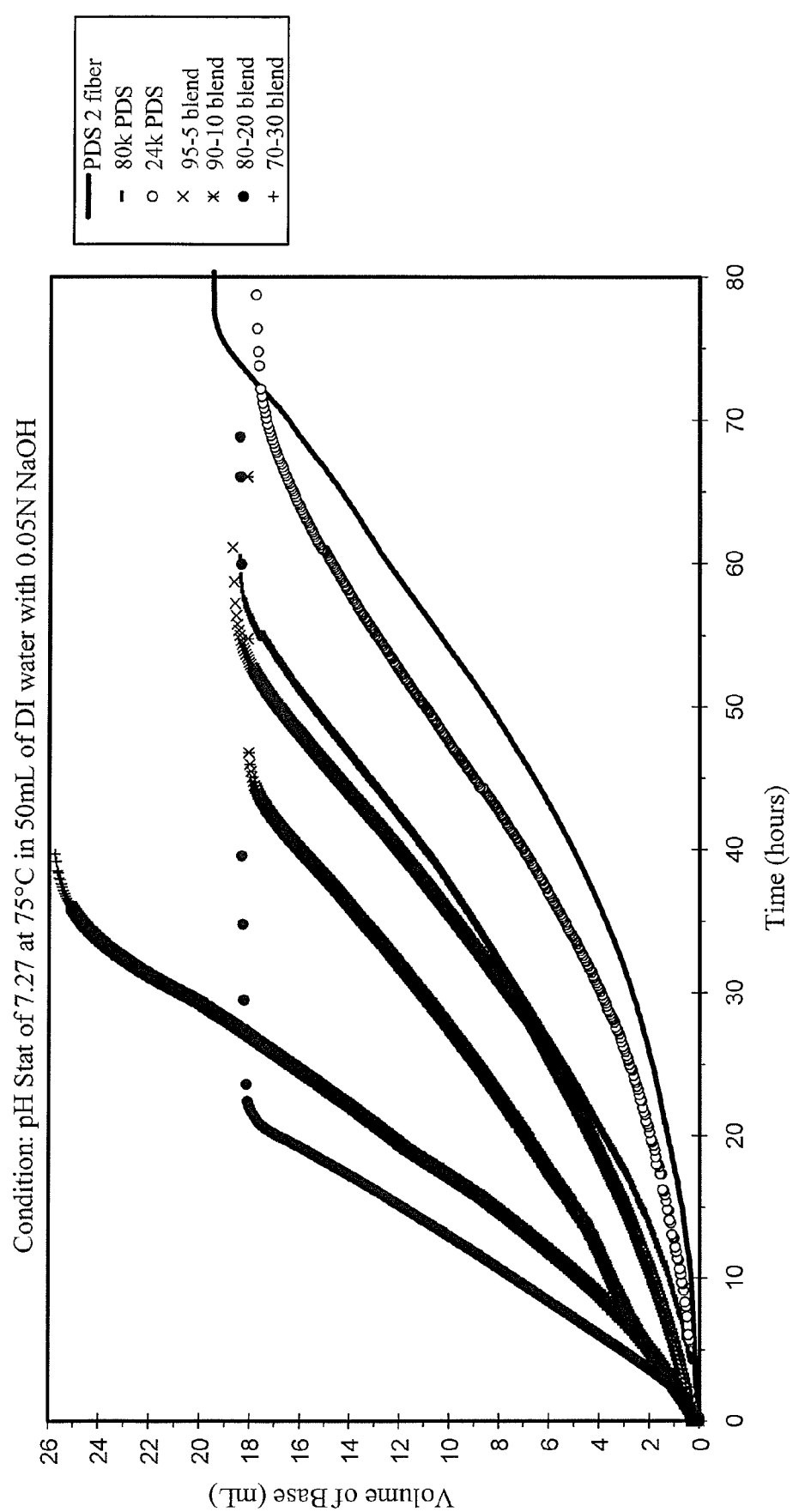
FIG. 10 presents hydrolysis profiles of a PDS II fiber monofilament, 80 k and 24 k PDS homopolymers, and various blends, including 95/5, 90/10, 80/20, and 70/30 compositions.

Hydrolysis measurements of PDS samples were carried on using the automated hydrolysis profile at 75° C., at a constant pH value of 7.27 (neutral) and a sodium hydroxide solution (0.05N) as a base. Prior to the experiments, all compression molded films were annealed using the same temperature condition, 70° C. for 10 minutes. Hydrolysis data were obtained for 80 k, and 24 k PDS homopolymers, as well as for various blends thereof. Data are presented in FIG. 10.

Again, considerably faster absorption profiles for all PDS blends were observed when compared to the monodisperse samples, with the 80/20 blend showing the greatest effect. PDS monofilament, on the other hand, exhibited the slowest hydrolysis rate, due to the high molecular orientation of both crystalline and amorphous chains, which makes water diffusion particularly more difficult.

Example 9

Enhanced Absorption Rates of Fully Amorphous PLGA 50/50 Copolymer Blends

Fully amorphous Poly(L-lactide-co-glycolide), PLGA 50/50 copolymers are used as a drug delivery matrix due to the absence of crystal morphology that may complicate the diffusion characteristics of materials and because of their relatively fast hydrolysis kinetics compared to PLLA or PGA homopolymers. However, there is a clear need to further increase the hydrolysis rate of the copolymer, especially in cases where faster initial drug concentration is required.

Hydrolysis measurements of PLGA 50/50 samples were conducted using an automated hydrolysis profile at 75° C., using a constant pH value of 7.27 (neutral) and a sodium hydroxide solution (0.05N) as a base. In this case, samples were not annealed since the materials are not capable of crystallizing. Some of the physical properties obtained on PLGA 50/50 copolymers, 60 k (Mw=60,000 Daltons), 10 k (Mw=10,000 Daltons) and their 70/30 wt. % blend are presented in Table 3.

Table 3 presents the physical properties of PLGA 50/50 copolymers having two distinct molecular weights and their 70/30 wt. % copolymer blend. During thermal analysis by DSC the samples were subjected to a heating rate of 10° C./min. No crystallinity (heat of fusion) was observed in any of the samples.

TABLE 3

Selected Physical Properties of PLGA 50/50 Copolymers

| Sample | IV (dL/g) | Tg (° C.) |
|---|---|---|
| 10k | 0.20 | 23.0 |
| 60k | 0.70 | 44.0 |
| 60k/10k 70/30 wt. % blend | NA | 40.0 |

Figure 11:
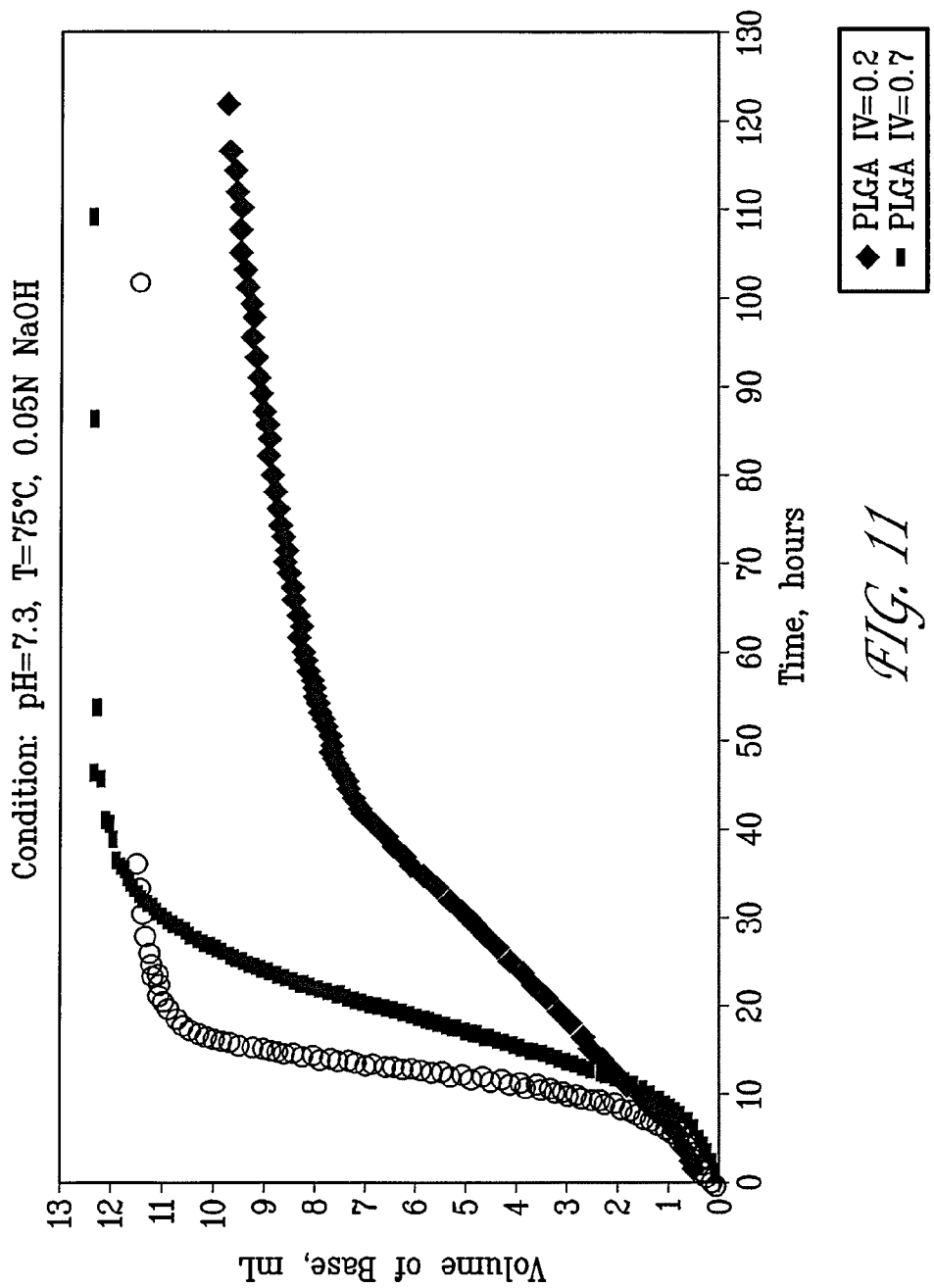
FIG. 11 presents hydrolysis profiles and demonstrates a faster absorption profile for a PLGA 50/50 copolymer blend than for the individual higher and lower molecular weight components.

Hydrolysis data shown in FIG. 11, demonstrated a faster absorption profile for the PLGA 50/50 copolymer blend than the individual higher and lower molecular weight components.

Example 10

Melt Blown Nonwoven Made from Bimodal PDS Polymer

On a six-inch melt blown nonwoven line of the type described hereinabove, equipped with single screw extruder, a bimodal PDS with 70% by weight of 80,000 Daltons weight-average molecular weight and 30% by weight of 24,000 Daltons weight-average molecular weight was extruded into melt blown nonwovens. This process involves feed the solid polymer pellets into a feeding hopper on an extruder. The extruder has a 1¼" single screw with three heating zones which gradually melt the polymer and extrude the molten polymer through a connector or transfer line. Finally, the molten polymer is pushing into a die assembly containing many capillary holes of which emerge small diameter fibers. The fiber diameter is attenuated at the die exit as the fiber emerges using high velocity hot air. About 6 inches from the die exit is a rotating collection drum on which the fibrous web is deposited and conveyed to a wind up spool. The melt blown line is of standard design as described by Buntin, Keller and Harding in U.S. Pat. No. 3,978,185, the contents of which are hereby incorporated by reference in their entirety. The die used had 210 capillary holes with a diameter of 0.014 inch per hole. The processing conditions and resulted properties of melt blown nonwovens are listed in the following table which follows.

TABLE 4

| | Inventive Examples | | |
|---|---|---|---|
| Sample | 1 | 2 | 3 |
| Processing Conditions: | | | |
| Die Temperature (° C.) | 187 | 194 | 195 |
| Die Pressure (psi) | 600 | 600 | 600 |
| Air Temperature (° C.) | 250 | 250 | 250 |
| Air Pressure (psi) | 22 | 22 | 22 |
| Extruder Speed (rpm) | 2.3 | 2.3 | 2.3 |

TABLE 4-continued

| | Inventive Examples | | |
|---|---|---|---|
| Sample | 1 | 2 | 3 |
| Throughput (grams/hole/minute) | 0.079 | 0.079 | 0.079 |
| Collector Speed (meters/minute) | 1.52 | 0.74 | 0.44 |
| Nonwoven Properties: | | | |
| Base Weight (gsm) | 35 | 72 | 121 |
| Fiber Diameter (μm) | 3.0-6.0 | 3.0-6.0 | 3.0-6.0 |
| Bust Strength (psi) | 4.25 | 10.50 | 16.00 |
| Peak Tensile (N) | 7.5 | 14.8 | 18.3 |
| Air Permeability (CFM) | 151.6 | 42.3 | 28.2 |
| Average Pore Size (μm) | 13.0 | 12.7 | 8.4 |

Thermal analysis conducted by DSC on the bimodal PDS melt blown nonwoven construct revealed the melting point of 107° C., and the heat of fusion of 60 J/g.

While the subject invention has been illustrated and described in detail in the drawings and foregoing description, the disclosed embodiments are illustrative and not restrictive in character. All changes and modifications that come within the scope of the invention are desired to be protected.

What is claimed is:

1. A medical device produced from a process comprising (i) the step of injection molding or extruding the medical device from a bimodal polymer composition or (ii) the step of subjecting a medical device made from said bimodal polymer composition to a heat treatment step; said bimodal polymer composition composing a blend of:
   (a) from about 60 to 80 wt % of a first component which is a semi-crystalline polylactide polymer having a first weight average molecular weight distribution between about 300,000 to about 2,000,000 Daltons; and
   (b) from about 20 to 40 wt % of a second component which is a semi-crystalline polytactide polymer having a second weight average molecular weight distribution between about 10,000 to about 50,000 Daltons, the weight average molecular weight ratio of said first molecular weight distribution to said second molecular weight distribution is at least about two to one;
   wherein said blend has an isothermal crystallization half time of less than that of either individual blend component over a temperature range of between about 130° C. to about 150° C. and a degree of crystallinity from about 10% to about 50% after said steps (i) or (ii).

2. The medical device of claim 1, wherein the medical device is selected from the group consisting of a suture, a clip, a staple, a pin, a screw, a fiber, a mesh, a clamp, a plate, a hook, a button, a snap, a prosthetic, a graft, an injectable polymer, a vertebrae disc, an anchoring device, a suture anchor, a septal occlusion device, an injectable defect filler, a preformed defect filler, a bone wax, a cartilage replacement, a spinal fixation device, a drug delivery device, a foam and a film.

3. A medical device produced from a process comprising (i) the step of injection molding or extruding the medical device from a bimodal polymer composition or (ii) the step of subjecting a medical device made from said bimodal polymer composition to a heat treatment step; said bimodal polymer composition composing a blend of;
   (a) from about 60 to 95 wt % of a first component which is a semi-crystalline poly(dioxanone) polymer having a first weight average molecular weight distribution between about 50,000 to about 100,000 Daltons; and
   (b) from about 5 to 40 wt % of a second component which is a semi-crystalline poly(dioxanone) polymer having a second weight average molecular weight distribution between about 10,000 to about 30,000 Daltons, the weight average molecular weight ratio of said first molecular weight distribution to said second molecular weight distribution is at least about two to one;
   wherein said blend has an isothermal crystallization half time of less than that of either individual blend component over a temperature range of between about 70° C. to about 80° C. and a degree of crystallinity of at least about 15% after said steps (i) or (ii).

4. The medical device of claim 3, wherein the medical device is selected from the group consisting of a suture, a clip, a staple, a pin, a screw, a fiber, a mesh, a clamp, a plate, a hook, a button, a snap, a prosthetic, a graft, an injectable polymer, a vertebrae disc, an anchoring device, a suture anchor, a septal occlusion device, an injectable defect filler, a preformed defect filler, a bone wax, a cartilage replacement, a spinal fixation device, a drug delivery device, a foam and a film.

5. A method of making a medical device, comprising (i)the step of injection molding or extruding said medical device from a bimodal polymer composition or (ii) the step of subjecting a medical device made from said bimodal polymer composition to a heat treatment step; said bimodal polymer composition comprising a blend of:
   (a) from about 60 to 80 wt % of a first component which is a semi-crystalline polylactide polymer having a first weight average molecular weight distribution between about 300,000 to about 2000,000 Daltons; and
   (b) from about 20 to 40 wt % of a second component which is a semi-crystalline potylactide polymer having a second weight average molecular weight distribution between about 10,000 to about 50,00 Daltons, the weight average molecular weight ratio of said first molecular weight distribution to said second molecular weight distribution is at least about two to one;
   wherein said blend has an isothermal crystallization half time of less than that of either individual blend component over a temperature range of between about 130° C. to about 150° C. and a degree of cristallinity from about 10% to about 50% after said steps (i) or (ii).

6. The method according to claim 5, where the first semi-crystalline poly(L-lactide) polymer has a first weight average molecular weight distribution between about 300,000 to about 500,000 Daltons.

7. The method according to claim 5, where the temperature range is between about 140° C. to about 150° C.

8. The method according to claim 5, wherein the blend is produced using a melt blending step.

9. The method according to claim 5, wherein the blend is produced in the presence of a solvent.

10. The method according to claim 9, wherein the solvent is selected from the group consisting of acetone, ethyl acetate, ethyl lactate, tetraethyleneglycol, chloroform, tetrahydrofuran, dimethyl sulfoxide, 1-methyl-2-pyrollidinone, dibutyl phthalate, methyl ethyl ketone, dibasic esters, methyl isobutyl ketone, dipropylene glycol, dichloromethane and hexafluoroisopropyl alcohol.

11. A method of making a medical device, comprising (i) the step of injection molding or extruding said medical device from a bimodal polymer composition or (ii) the step of subjecting a medical device made from said bimodal polymer composition to a heat treatment step; said bimodal polymer composition comprising a blend of:
   (a) from about 60 to 95 wt % of a first component which is a semi-crystalline poly(dioxanone) polymer having a first weight average molecular weight distribution between about 50.000 to about 100,000 Daltons; and (b) from about 5 to 40 wt % of a second amount of a semi-crystalline poly(dioxanone) polymer having a second weight average molecular weight distribution between about 10,000 to about 50,000 Daltons, the weight average molecular weight ratio of said first molecular weight distribution to said second molecular weight distribution is at least about two to one;

wherein said blend has an isothermal crystallization half time of less than that of either individual blend component over a temperature range of between about 70° C. to about 80° C. and a degree of crystallinity of at least about 15% after said steps(i) or (ii).

12. The method according to claim 11, wherein the blend is produced using a melt blending step.

13. The method according to claim 11, wherein the blend is produced in the presence of a solvent.

14. The method according to claim 13, wherein the solvent is selected from the group consisting of acetone, ethyl acetate, ethyl lactate, tetraethyleneglycol, chloroform, tetrahydrofuran, dimethyl sulfoxide, 1-methyl-2-pyrollidinone, dibutyl phthalate, methyl ethyl ketone, dibasic esters, methyl isobutyl ketone, dipropylene glycol, dichloromethane and hexafluoroisopropyl alcohol.

* * * * *